(12) United States Patent
Drmanac et al.

(10) Patent No.: US 10,726,942 B2
(45) Date of Patent: Jul. 28, 2020

(54) LONG FRAGMENT DE NOVO ASSEMBLY USING SHORT READS

(71) Applicant: Complete Genomics, Inc., Mountain View, CA (US)

(72) Inventors: Radoje Drmanac, Los Altos Hills, CA (US); Bahram Ghaffarzadeh Kermani, Los Altos, CA (US)

(73) Assignee: Complete Genomics, Inc., San Jose, CA (US)

( * ) Notice: Subject to any disclaimer, the term of this patent is extended or adjusted under 35 U.S.C. 154(b) by 1431 days.

(21) Appl. No.: 14/467,797

(22) Filed: Aug. 25, 2014

(65) Prior Publication Data

US 2015/0057947 A1 Feb. 26, 2015

Related U.S. Application Data

(60) Provisional application No. 61/869,570, filed on Aug. 23, 2013.

(51) Int. Cl.
*G16B 30/00* (2019.01)
*G16B 30/20* (2019.01)

(52) U.S. Cl.
CPC ............. *G16B 30/00* (2019.02); *G16B 30/20* (2019.02)

(58) Field of Classification Search
None
See application file for complete search history.

(56) References Cited

U.S. PATENT DOCUMENTS

| 5,577,249 A | 11/1996 | Califano |
| 5,795,782 A | 8/1998 | Church et al. |
| 6,015,714 A | 1/2000 | Baldarelli et al. |
| 6,055,526 A | 4/2000 | Ambroziak |
| 6,210,891 B1 | 4/2001 | Nyren et al. |
| 6,306,597 B1 | 10/2001 | Macevicz |

(Continued)

FOREIGN PATENT DOCUMENTS

| CN | 102477460 A | 5/2012 |
| CN | 102841987 A | 12/2012 |

(Continued)

OTHER PUBLICATIONS

International Preliminary Report on Patentability of PCT/US2014/052572 dated Mar. 3, 2016, 16 pages.

(Continued)

*Primary Examiner* — Olivia M. Wise
(74) *Attorney, Agent, or Firm* — Kilpatrick Townsend & Stockton LLP

(57) ABSTRACT

Techniques perform de novo assembly. The assembly can use labels that indicate origins of the nucleic acid molecules. For example, a representative set of labels identified from initial reads that overlap with a seed can be used. Mate pair information can be used. A sequence read that aligns to an end of a contig can lead to using the other sequence read of a mate pair, and the other sequence read can be used to determine which branch to use to extend, e.g., in an external cloud or helper contig. A kmer index can include labels indicating an origin of each of the nucleic acid molecules that include each kmer, memory addresses of the reads that correspond to each kmer in the index, and a position in each of the mate pairs that includes the kmer. Haploid seeds can also be determined using polymorphic loci identified in a population.

32 Claims, 20 Drawing Sheets

Specification includes a Sequence Listing.

(56) References Cited

U.S. PATENT DOCUMENTS

| | | |
|---|---|---|
| 6,309,824 B1 | 10/2001 | Drmanac |
| 6,401,043 B1 | 6/2002 | Stanton et al. |
| 6,401,267 B1 | 6/2002 | Drmanac |
| 6,403,312 B1 | 6/2002 | Dahiyat et al. |
| 6,627,067 B1 | 9/2003 | Branton et al. |
| 6,653,072 B1 | 11/2003 | Patten et al. |
| 6,775,622 B1 | 8/2004 | Holloway |
| 6,828,100 B1 | 12/2004 | Ronaghi |
| 6,833,246 B2 | 12/2004 | Balasubramanian |
| 6,864,052 B1 | 3/2005 | Drmanac et al. |
| 6,911,345 B2 | 6/2005 | Quake et al. |
| 7,058,515 B1 | 6/2006 | Selifonov et al. |
| 7,238,485 B2 | 7/2007 | Akeson et al. |
| 7,258,838 B2 | 8/2007 | Li et al. |
| 7,329,496 B2 | 2/2008 | Dower et al. |
| 2002/0182630 A1 | 12/2002 | Milosavljevic |
| 2003/0064382 A1 | 4/2003 | Preparata et al. |
| 2003/0186226 A1 | 10/2003 | Brennan et al. |
| 2003/0235854 A1 | 12/2003 | Chan et al. |
| 2004/0018525 A1 | 1/2004 | Wirtz et al. |
| 2004/0197917 A1 | 10/2004 | Carozzi et al. |
| 2005/0112590 A1 | 5/2005 | Boom et al. |
| 2005/0149272 A1 | 7/2005 | Pe'er et al. |
| 2005/0187916 A1 | 8/2005 | Levin et al. |
| 2005/0202501 A1 | 9/2005 | Yamamoto et al. |
| 2006/0073501 A1 | 4/2006 | Van Den Boom et al. |
| 2006/0286566 A1 | 12/2006 | Lapidus et al. |
| 2006/0287833 A1 | 12/2006 | Yakhini |
| 2007/0099208 A1 | 5/2007 | Drmanac et al. |
| 2007/0122817 A1 | 5/2007 | Church et al. |
| 2007/0225918 A1 | 9/2007 | Sayood et al. |
| 2008/0040045 A1 | 2/2008 | Selifonov et al. |
| 2008/0234136 A1 | 9/2008 | Drmanac et al. |
| 2008/0256070 A1 | 10/2008 | Inglis |
| 2008/0279892 A1 | 11/2008 | Jin et al. |
| 2008/0318795 A1 | 12/2008 | Selifonov et al. |
| 2009/0029477 A1 | 1/2009 | Meller et al. |
| 2009/0075343 A1 | 3/2009 | Sparks et al. |
| 2009/0111115 A1 | 4/2009 | Drmanac et al. |
| 2009/0111705 A1 | 4/2009 | Sparks et al. |
| 2009/0111706 A1 | 4/2009 | Sparks et al. |
| 2009/0264299 A1 | 10/2009 | Drmanac et al. |
| 2011/0004413 A1 | 1/2011 | Carnevali et al. |
| 2013/0059740 A1 | 3/2013 | Drmanac et al. |
| 2013/0124100 A1 | 5/2013 | Drmanac et al. |
| 2013/0203605 A1 | 8/2013 | Shendure et al. |

FOREIGN PATENT DOCUMENTS

| | | |
|---|---|---|
| WO | 2006/073504 A2 | 7/2006 |
| WO | 2007/120208 A2 | 10/2007 |
| WO | 2009/155443 A2 | 12/2009 |
| WO | 2010/091021 A2 | 8/2010 |
| WO | 2010/091023 A2 | 8/2010 |
| WO | 2010/091024 A1 | 8/2010 |
| WO | 2010/127045 A2 | 11/2010 |

OTHER PUBLICATIONS

International Search Report and Written Opinion dated Dec. 23, 2014 in PCT/US2014/052572, 19 pages.
Miller, Jason, R., et al., "Assembly Algorithms for Next-Generation Sequencing Data," Genomics, Jun. 2010, vol. 95, No. 6, pp. 315-327.
Pevzner, et al., "De Novo Repeat Classification and Fragment Assembly," Genome Res., 2004, vol. 14, pp. 1786-1796.
Medvedev, et al., "Maximum Likelihood Genome Assembly," Journal of Computational Biology, 2009, vol. 16, pp. 1101-1116.
Marth, et al., "A general approach to single-nucleotide polymorphism discovery," Nature Genetics, 1999, vol. 23, pp. 452-456.
Li, et al., "Mapping short DNA sequencing reads and calling variants using mapping quality scores," Genome Research, 2008, vol. 18, pp. 1851-1858.
Office Action dated Sep. 5, 2013 in Chinese Application No. 201080029207.1, 11 pages (English Translation).
International Search Report and Written Opinion corresponding to the PCT application No. PCT/US10/22907, dated Nov. 30, 2010, 9 pages total.
International Search Report and Written Opinion corresponding to the PCT application No. PCT/US10/22912, dated Jun. 23, 2010, 9 pages total.
International Search Report and Written Opinion corresponding to the PCT application No. PCT/US10/22913, dated Mar. 16, 2010, 9 pages total.
International Search Report and Written Opinion corresponding to the PCT application No. PCT/US10/32851, dated Nov. 18, 2010, 13 pages total.
Annexstein, "*Generating De Bruifn Sequences: An Efficient Implementation*", IEEE Transactions on Computers, Feb. 1997, (Retrieved from the Internet on Nov. 1, 2010<URL:http://www.computer.org> 46(2):198-200).
Chan et al., "*On the Complexities of de Bruijn Sequences*". Journal of Combinatorial Theory, Series A 1982, 33(3):233-246.
Dahiyat et al., "*De Novo Protein Design: Fully Automated Sequence Selection*", Science 1997, 278 (5335):82-87.
Flicek et al., "*Sense From Sequence Reads: Methods for Alignment and Assembly*" Nature Methods Supplement Oct. 15, 2009, 6(11S):S6-S12.
Gonnet et al., "*Exhaustive Matching of the Entire Protein Sequence Database*", Science 1992, 256(5062):1443-1445.
Han al el., "*SPIDER: Software for Protein Identification From Sequence Tags With De Novo Sequencing Error*", 2004 IEEE Computational Systems Bioinformatics Conference 2004. (Retrieved from the Internet on Nov. 1, 2010: <URL: http://citeseerx.ist.psu.edu/viewdoc/download?doi=10.1.1.71.8935&rep=rep1&type=pdf>) p. 1-18.
Margulies et al, "*Genome Sequencing in Microfabricated High-Density Picolitre Reactors*", Nature 2005, 437:376-380.
Ning at al., "*SSAHA: A Fast Search Method for Large DNA Databases*", pp. 1725-1729, Genome Research 2001,11(10):1725-1729.
Pevzner et al. "*An Eulerian Path Approach to DNA Fragment Assembly*", Proceedings of the National Academy of Sciences 2001, 98(17):9748-9753.
Ronaghi et al., "*Real-Time DNA Sequencing Using Detection of Pyrophosphate Release*", Anal. Biochem, 1996, 242:84-89.
Webb et al. "*BALSA: Bayesian Algorithm for Local Sequence Alignment*" Nucleic Acids Research 2002, 30(5), pp. 1268-1277.
Zerbino et al. "*Velvet: Algorithms for De Novo Short Read Assembly Using De Bruijn Graphs*", Genome Research 2008, 18(5), pp. 821-829.
Li, R. et al. "De Novo Assembly of Human Genomes With Massively Parallel Short Read Sequencing." *Genome Research*, vol. 20. Published Dec. 17, 2009. pp. 265-272.
Niu, B et al. "Alignment and Assembly Algorithm Based on New Sequencing Technology." Computer Engineering, vol. 35, No. 20. Published Dec. 31, 2009. 3 pages.
Translation of Chinese Office Action received in Chinese Patent Application No. 201480056125.4, dated Jul. 17, 2018. 26 pages.
Translation of Chinese Office Action received in Chinese Patent Application No. 201480056125.4, dated Apr. 11, 2019. 6 pages.
Translation of Chinese Office Action received in Chinese Patent Application No. 201480056125.4, dated Oct. 9, 2019, 6 pages.

K-mer index 400
| 12-mer | 1st Read # | 2nd Read # | 3rd Read # |
|---|---|---|---|
| AAAAAAAAAAAA | 10 | 150 | 10,534 |
| AAAAAAAAGATA | 84 | 22,654 | - |
| ⋮ | | | |
| AATGCGTAGCTA | 920 | - | - |
| ⋮ | | | |
...
FIG. 4A
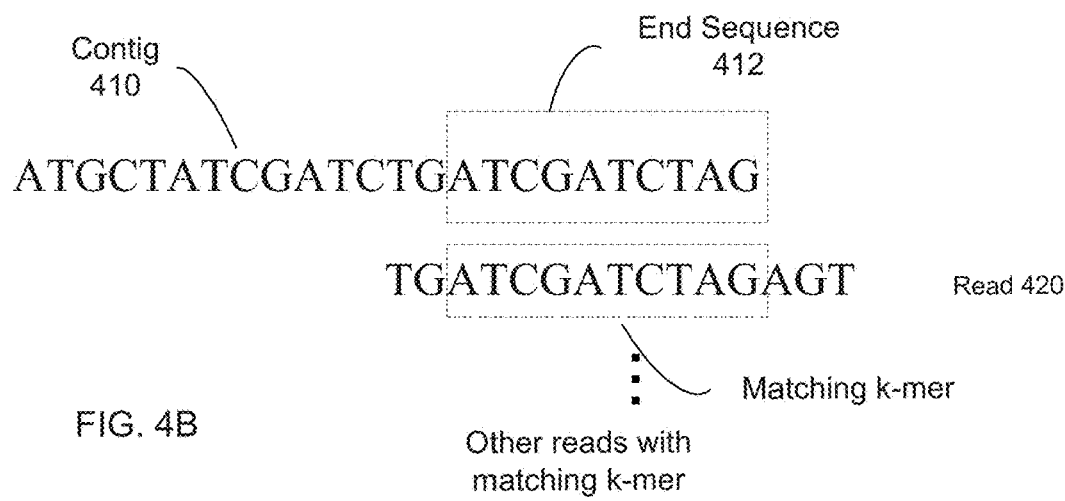
FIG. 4B
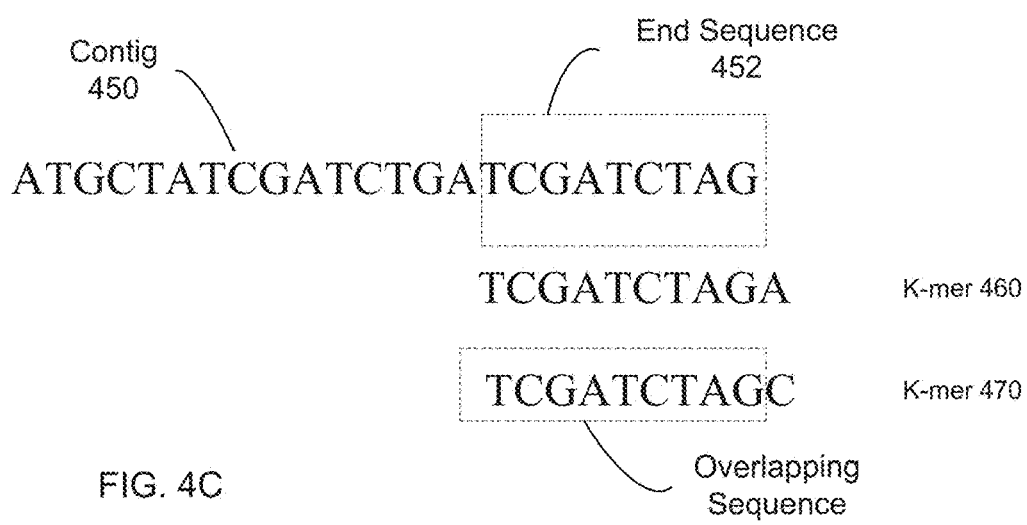
FIG. 4C

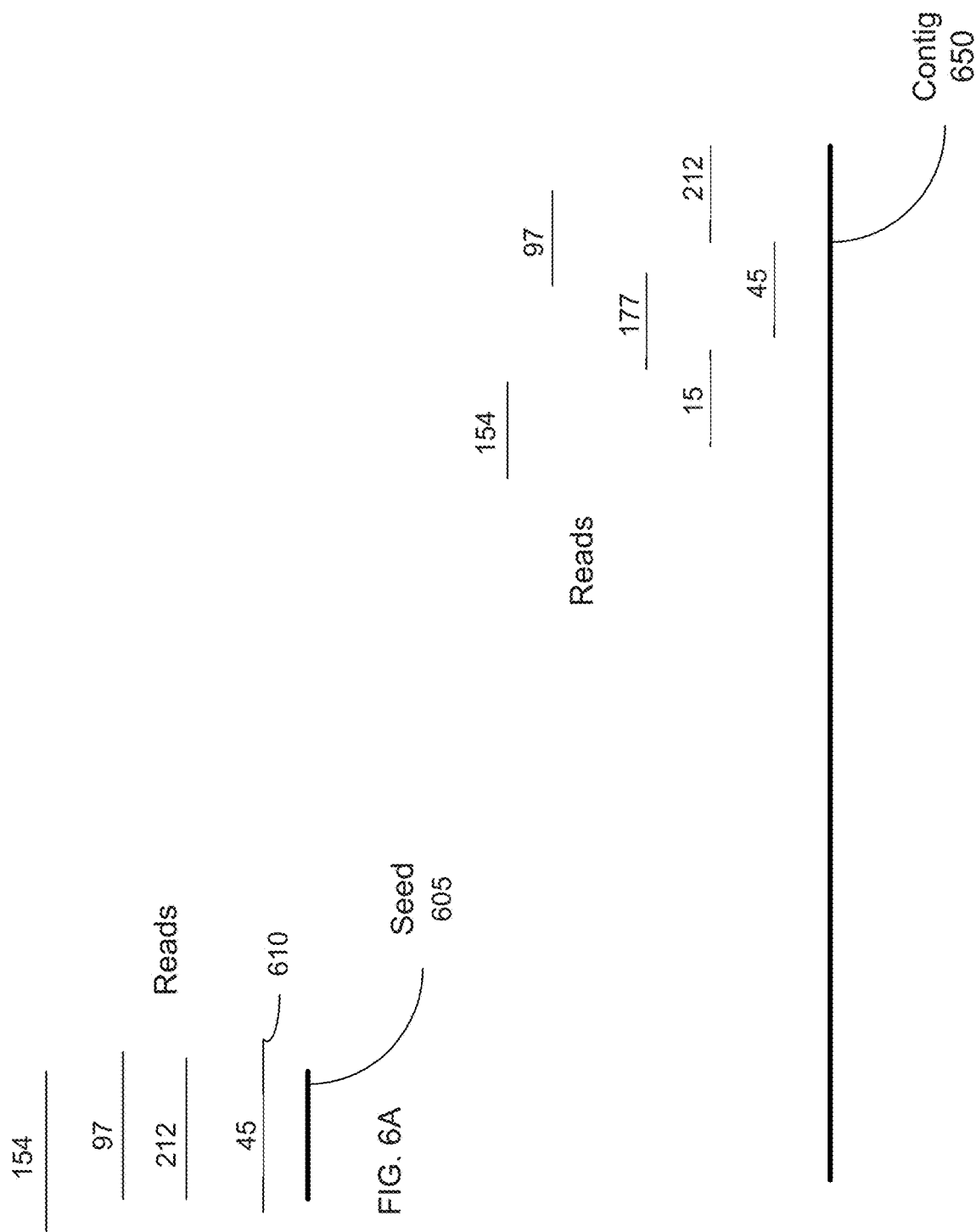

700

| 710 | Receive sequence data from a sequencing of a plurality of nucleic acid molecules of the organism, the sequence data for each molecule including a label indicating an original of the molecule |

| 720 | Receive a first contig of the first chromosomal region |

| 730 | Extend the first contig using a group of sequence reads that overlap with an end sequence of the first contig, the group including sequence reads with a plurality of different labels indicating different origins |

FIG. 7

Mate Pair 910

1500

1501

| K-mer | 1st Read Address | 2nd Read Address | 3rd Read Address | 4th Read Address |
|---|---|---|---|---|
| k-mer 1 | 102 | 120,700 | 502,458 | 5,700,856 |
| k-mer 2 | 4,012 | 250,445 | - | - |
| ⋮ | | | | |
| K-mer 100,000 | 254 | 12,456 | - | - |
| ⋮ | | | | |

| K-mer | Read #/ address | Position in read | Read #/ address | Position in read |
|---|---|---|---|---|
| k-mer 1 | 102 | 3 | 502,458 | 26 |
| k-mer 2 | 4,012 | 1 | - | - |
| ⋮ | | | | |
| K-mer 100,000 | 254 | 2 | - | - |
| ⋮ | | | | |

| kmer | Read #/address | Label | Position in read | 2nd Read #/address | Label | Position in read |
|---|---|---|---|---|---|---|
| k-mer 1 | 102 | 23 | 3 | 502,458 | 41 | 4 |
| k-mer 2 | 4,012 | 65 | 1 | 10,668 | 4 | 2 |
| . . . | | | | | | |
| K-mer 100,000 | 254 | 23 | 2 | 2,823 | 245 | 26 |

SEQUENCE LISTING

<160> NUMBER OF SEQ ID NOS: 14

<210> SEQ ID NO 1
<211> LENGTH: 24
<212> TYPE: DNA

```
<213> ORGANISM: Artificial Sequence
<220> FEATURE:
<223> OTHER INFORMATION: synthetic Contig 110, Contig 150, Contig 410,
      Contig 450, diploid Contig 510, Contig 550, Contig 580

<400> SEQUENCE: 1
atgctatcga tctgatcgat ctag                                            24

<210> SEQ ID NO 2
<211> LENGTH: 10
<212> TYPE: DNA
<213> ORGANISM: Artificial Sequence
<220> FEATURE:
<223> OTHER INFORMATION: synthetic end sequence extended by sequence
      read, Sequence Read 120, Sequence Read 160, K-mer 460, K-mer 520,
      K-mer 560

<400> SEQUENCE: 2
tcgatctaga                                                            10

<210> SEQ ID NO 3
<211> LENGTH: 10
<212> TYPE: DNA
<213> ORGANISM: Artificial Sequence
<220> FEATURE:
<223> OTHER INFORMATION: synthetic end sequence extended by sequence
      read, Sequence Read 170, K-mer 470, K-mer 525

<400> SEQUENCE: 3
tcgatctagc                                                            10

<210> SEQ ID NO 4
<211> LENGTH: 12
<212> TYPE: DNA
<213> ORGANISM: Artificial Sequence
<220> FEATURE:
<223> OTHER INFORMATION: synthetic 12-mer from K-mer index

<400> SEQUENCE: 4
aaaaaaaaaa aa                                                         12

<210> SEQ ID NO 5
<211> LENGTH: 12
<212> TYPE: DNA
<213> ORGANISM: Artificial Sequence
<220> FEATURE:
<223> OTHER INFORMATION: synthetic 12-mer from K-mer index

<400> SEQUENCE: 5
aaaaaaaaga ta                                                         12

<210> SEQ ID NO 6
<211> LENGTH: 12
<212> TYPE: DNA
<213> ORGANISM: Artificial Sequence
<220> FEATURE:
<223> OTHER INFORMATION: synthetic 12-mer from K-mer index

<400> SEQUENCE: 6
aatgcgtagc ta                                                         12

<210> SEQ ID NO 7
<211> LENGTH: 15
<212> TYPE: DNA
<213> ORGANISM: Artificial Sequence
<220> FEATURE:
<223> OTHER INFORMATION: synthetic Sequence Read 420
```

<400> SEQUENCE: 7
tgatcgatct agagt                                                    15

<210> SEQ ID NO 8
<211> LENGTH: 25
<212> TYPE: DNA
<213> ORGANISM: Artificial Sequence
<220> FEATURE:
<223> OTHER INFORMATION: synthetic Haploid Contig 530

<400> SEQUENCE: 8
atgctatcga tctgatcgat ctaga                                         25

<210> SEQ ID NO 9
<211> LENGTH: 25
<212> TYPE: DNA
<213> ORGANISM: Artificial Sequence
<220> FEATURE:
<223> OTHER INFORMATION: synthetic Haploid Contig 535

<400> SEQUENCE: 9
atgctatcga tctgatcgat ctagc                                         25

<210> SEQ ID NO 10
<211> LENGTH: 18
<212> TYPE: DNA
<213> ORGANISM: Artificial Sequence
<220> FEATURE:
<223> OTHER INFORMATION: synthetic Sequence Read 591

<400> SEQUENCE: 10
tcgatctaga gtcttgcc                                                 18

<210> SEQ ID NO 11
<211> LENGTH: 18
<212> TYPE: DNA
<213> ORGANISM: Artificial Sequence
<220> FEATURE:
<223> OTHER INFORMATION: synthetic Sequence Read 592

<400> SEQUENCE: 11
tcgatctagc gtcttgcc                                                 18

<210> SEQ ID NO 12
<211> LENGTH: 18
<212> TYPE: DNA
<213> ORGANISM: Artificial Sequence
<220> FEATURE:
<223> OTHER INFORMATION: synthetic Sequence Read 593

<400> SEQUENCE: 12
atctagcgtc ttgccttg                                                 18

<210> SEQ ID NO 13
<211> LENGTH: 15
<212> TYPE: DNA
<213> ORGANISM: Artificial Sequence
<220> FEATURE:
<223> OTHER INFORMATION: synthetic Sequence Read 594

<400> SEQUENCE: 13
tagcgtcttg ccttg                                                    15

<210> SEQ ID NO 14
<211> LENGTH: 12
<212> TYPE: DNA
<213> ORGANISM: Artificial Sequence
<220> FEATURE:

```
<223> OTHER INFORMATION: synthetic 12-mer from K-mer index, second
       12-mer

<400> SEQUENCE: 14
aaaaaaaaaa ac                                                              12
```

LONG FRAGMENT DE NOVO ASSEMBLY USING SHORT READS

CROSS-REFERENCES TO RELATED APPLICATIONS

This application claims the benefit of U.S. Provisional Application No. 61/869,570, filed Aug. 23, 2013, the entirety of which is incorporated by reference herein.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-33-1.TXT, created on Sep. 8, 2014, 4,096 bytes, machine format IBM-PC, MS-Windows operating system, is hereby incorporated by reference in its entirety for all purposes.

FIELD

The present disclosure generally relates to genomic sequencing, and more specifically to de novo assembly of sequence reads.

BACKGROUND

In genomic sequencing, nucleic acid molecules of an organism are sequenced to provide sequence reads. A sequencing read is typically aligned (mapped) to a reference genome as part of determining the genome of the organism. In this manner, differences between the genome of the organism and a reference genome can be identified.

However, such mapping to the reference genome can lead to errors. The mapping to the reference genome can bias the results, thereby leading to errors. For example, insertions and deletions in a genome are very hard to map to the reference genome, and thus may be inaccurate and/or time consuming.

De novo assembly uses information from the sequence reads to align the sequence reads to each other. But, de novo assembly is typically reserved for small (local) regions of the genome that had been identified as problematic after mapping to the reference genome. The techniques used for local de novo assembly suffer drawbacks if they were applied to de novo assembly of the entire genome, or at least a substantial part of the genome.

Therefore, it is desirable to provide new techniques de novo assembly.

BRIEF SUMMARY

Embodiments relate to methods for performing de novo assembly. For example, sequence reads can have a label indicating an origin of the nucleic acid molecule. A label can correspond to one of a plurality of wells so that an origin of a sequence read can be tracked. Each label can correspond to a portion of a genome (e.g., with less than one genomic equivalent of DNA corresponding to each well). Labels corresponding to a same region can be identified, e.g., by having reads that align to a same contig. When assembling a contig, the contig can be extended using sequence reads with a plurality of different labels (e.g., a representative set of labels identified from initial reads that overlap with a seed).

In another example, mate pair information can be used. A first group of sequence reads can be identified that align to an end of a contig, and the mate pairs of these identified sequence reads can be determined. The other sequence reads of the mate pairs can be used to determine a subgroup of the first group, where the contig is extended using the first subgroup of sequence reads. For instance, the other sequence reads can be first sequence reads and compared to the contig. The best matching other sequence reads correspond to the correct first subgroup to extend the contig. The other sequence reads can also be compared to a set of second sequence reads that known to occur past the end of the contig, e.g., in an external cloud or helper contig. Label information and mate pair information can both be used.

In yet another example, a kmer index can be created, where the index includes an entry for each kmer, and each entry includes labels indicating an origin of each of the nucleic acid molecules that includes that kmer. A specific set of labels can be used to retrieve sequence reads corresponding to a kmer that overlaps with an end sequence of the contig. In yet another example, a kmer index stores memory addresses of the reads that correspond to each kmer in the index. In yet another example, for each kmer in a kmer index, the index stores a position in each of the mate pairs that includes the kmer.

In yet another example, haploid seeds are created, each for creating a haploid contig. The haploid seeds can be created by accessing a database to retrieve one or more polymorphic loci identified in a population (e.g., a population of humans). The sequence reads can be analyzed to determine whether a locus is heterozygous for the organism being tested. If a locus is heterozygous, a locus might be used for creating the two haploid seeds. A first haploid seed can be created using reads that map to the first locus and that have a first allele. A second haploid seed can be created using reads that map to the first locus and that have a second allele. The two seeds can then be extended, where only one branch is chosen for each extension of a haploid seed.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 4A shows an example k-mer index, where the k-mer length is 12 (SEQ ID NOS:4-6). FIG. 4B is a diagram showing a read (SEQ ID NO:7) including a k-mer that matches to the end sequence. Contig 410=SEQ ID NO:1. FIG. 4C is a diagram showing an end sequence of length 9 (K−1) and two k-mers of length 10 (SEQ ID NOS:2 and 3). Contig 450=SEQ ID NO:1.

FIG. 6A shows an example for how a representative set of labels may be created for a seed sequence. FIG. 6B shows an example for how a representative set of labels may be updated and maintained for contig.

FIG. 7 shows a method 700 for assembling a sequence of a first chromosomal region of an organism using labels according to embodiments of the present invention.

FIG. 15A shows an example k-mer index with read addresses stored for each k-mer according to embodiments of the present invention. FIG. 15B shows an example k-mer index with read addresses stored for each k-mer according to embodiments of the present invention.

FIG. 16 shows an example k-mer index with read labels stored for each k-mer according to embodiments of the present invention.

DEFINITIONS

Figure 1A:
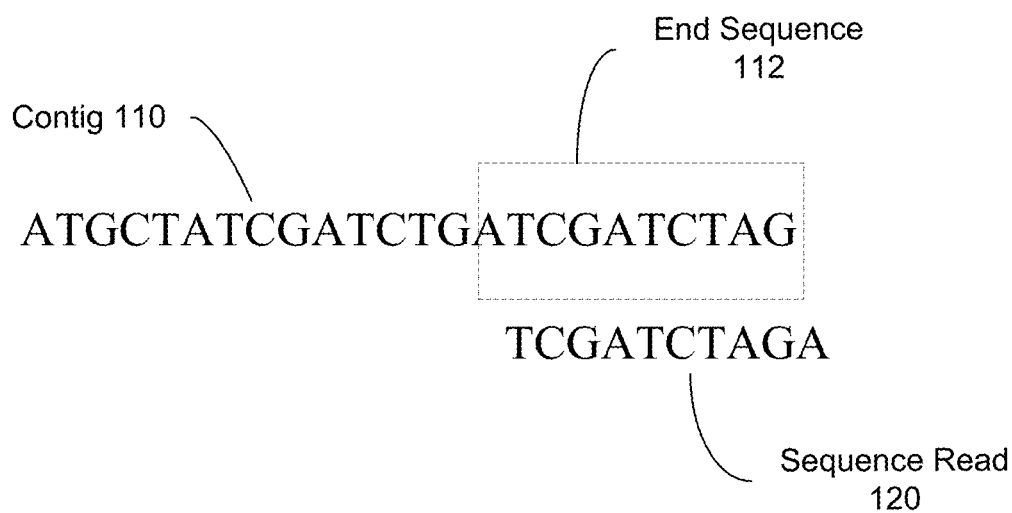
FIG. 1A shows an example of a contig (SEQ ID NO:1) with an end sequence being extended by sequence read (SEQ ID NO:2).

The following definitions may be helpful in providing background for an understanding of embodiments of the invention.

A "sequence read" or "read" refers to data representing a sequence of monomer units (e.g., bases) that comprise a nucleic acid molecule (e.g., DNA, cDNA, RNAs including mRNAs, rRNAs, siRNAs, miRNAs and the like). The sequence read can be measured from a given molecule via a variety of techniques. Clonal reads (e.g., resulting from amplification) correspond to the same nucleic acid molecule. In one aspect, clonal reads do not contain more information than the representative read, and can be removed, if encountered. Effective reads are from unique polynucleotides, e.g., after removal of clonal reads. Alternatively, in lieu of removing, the clonal reads can be combined to one representative read, which can have higher accuracy than any of the constituents, e.g., by picking bases with the highest score.

A "fragment" refers to a nucleic acid molecule that is in a biological sample. Fragments can be referred to as long or short, e.g., fragments longer than 10 Kb (e.g. between 50 Kb and 100 Kb) can be referred to as long, and fragments shorter than 2000 bases can be referred to as short. A long fragment can be broken up into short fragments, upon which sequencing is performed.

A "mate pair" or "mated reads" or "paired-end" can refer to any two reads from a same molecule that are not fully overlapped (i.e., cover different parts of the molecule). Each of the two reads would be from different parts of the same molecule, e.g., from the two ends of the molecule. As another example, one read could be for one end of the molecule in the other read for a middle part of the molecule. As a genetic sequence can be ordered from beginning to end, a first read of a molecule can be identified as existing earlier in a genome than the second read of the molecule when the first read starts and/or ends before the start and/or end of the second read. Two reads can be referred to as being different arm reads when the two reads are from different parts of the same molecule. More than two reads can be obtained for each molecule, where each read would be for different part of the molecule. Usually there is a gap (mate gap) from about 100-10,000 bases of unread sequence between two reads. Examples of mate gaps include 500+/−200 bases and 1000+/−300 bases.

The small fragments that originate from a same long fragment can have a same "label" that identifies an origin for small fragment. An example of a label is "Well ID," which refers to a bar code or tag that is added to a small fragment to determine which well the read comes from. Such an example is applicable when long fragments are distributed into multiple wells, or other types of aliquots, and then fragmented into smaller fragments. A tag for each read is decoded (corrected) and projected into a unique tag. Another example of a label can be found in U.S. Provisional Application No. 61/801,052, where a same label can be affixed to different segments of a same long fragment.

Effective wells (EW), or labels, correspond to the labels for non-clonal reads, e.g., first the clonal reads are found and removed, and then the wells corresponding to those reads are reported. Neighborhood wells (NW), or labels, correspond to labels of reads that are expected to be in proximity (e.g., a specified distance or diameter) of a current sequence that is being assembled. Effective neighborhood wells (ENW), or labels, correspond to labels of non-clonal reads that are representative of the current contig. The neighborhood diameter can be related to the fragment size, which may be much larger than the contig size; therefore in those cases, the whole contig may be considered to be one neighborhood.

A "seed sequence" corresponds to the first sequence used to start an assembly process. An "initial sequence" corresponds to any sequence that is extended at any part of the assembly process. An "extended sequence" results from extending the seed sequence (or other initial sequence) by any number of bases. A "contig" can correspond to any of the sequences at the beginning (initial) or end (extended) of an iteration of an assembly process. A contig can be a contiguous piece of reconstructed DNA. A super-contig refers to a larger contig made by concatenation of the original contigs, e.g., via a stitching algorithm.

A short contig structure (SCS) can refer to a contig that is less than the size of the genomic region spanned by a mate pair, e.g., less than 1000 bases. A long contig structure (LCS) can refer to a contig that is more than the nominal size/length of a mate. A diploid contig (DC or DipCon) refers to a contig where the phase of the two haplotypes on it are unknown. A haploid contig (HC or HapCon) refers to a contig that has been established into two haplotypes in the genome is diploid. Thus, two haploid contigs would result. A diploid contig can be unzipped to obtain the two haploid contigs.

A "k-mer" is a sequence of K bases. Example values for K includes values between 14 and 150. A sequence read may be decomposed into multiple k-mers. For example, a read of length 30 can be decomposed into 11 contiguous k-mers of length 20. The k-mers can also be created from non-contiguous bases, i.e., there can be a gap. For example, 10 bases, skip 2, and then the next 10 bases to obtain a 20-mer. A "k-mers index" (also referred to as an index) corresponds to a data structure (e.g., a tree structure) that organizes k-mers for easier access. An index can be stored in a direct way or in a similar manner as a sparse matrix, e.g., each row can be a unique k-mer with the stored columns corresponding to reads that include the unique k-mer. An assembly process can use k-mers and a k-mer index to determine alignments between sequence reads.

A "cloud" is a collection of sequences from the reads, and may be stored as an index. The sequences can be the whole reads or particular k-mers (subsets) thereof. An "internal cloud" can correspond to sequences from reads that been used to build a current contig. An "external cloud" can correspond to second reads of mate pairs whose first reads have been used to build the current contig.

A "branch" corresponds to different options for extending a contig at an end sequence. For example, different branches can indicate different bases for extending the contig, which may be extended by one or more bases. A sub-branch refers to reads that are part of the same branch (e.g., indicate a same extension), but whose other reads of a mate pair correspond to different regions of the genome.

DETAILED DESCRIPTION

De novo assembly uses information from the sequence reads to align the sequence reads to each other. Various aspects of de novo assembly are described. For example, a label can indicate an origin of the nucleic acid molecule, e.g., a well that the nucleic acid molecule is from. Nucleic acid molecules with a same label are more likely to be from a same long fragment that is being reconstructed as part of the assembly process. A contig can be built from a representative set of labels, e.g., a set determined by aligning reads to a seed.

The extension of a contig can involve a kmer index. Branches (sequence hypotheses) for extension can be chosen based on evidence of overlapping reads. Multiple levels of overlapping can be used, e.g., aligning reads to each other before selecting a branch. Kmer indexes can be created in various ways and created with various information, such information includes labels, memory addresses of reads associated with a kmer, and position in a mate pair.

A seed sequence can be created in various ways. And, haploid seeds can be created around known polymorphic loci that exhibit heterozygosity in the test organism.

Mate pair information can be used to select which branch for extension. For example, the non-aligning read of a mate pair (i.e., not aligning to an end of a contig) can be compared to an internal cloud, an external cloud, or a helper contig. Such a comparison can provide consistency among reads for extension, thereby providing greater accuracy. Further details are described below.

I. Simple Extension

The basic concept of extending a contig is described. Assume that one starts with the short contig of 24 bases, such as ATGCTATCGATCTGATCGATCTAG (SEQ ID NO:1). If one were extending to the right, an end sequence could be taken as the last 10 bases, which would be ATCGATCTAG (SEQ ID NO:2). A sequence read of 10 bases can be considered overlap/align with the end sequence when the last nine bases of the end sequence match the first nine bases of the sequence read. The $10^{th}$ base of the sequence read can indicate which base is next in the genome.

In other examples, the sequence read could be longer (or even shorter), as could the end sequence. The overlap of the bases may also not be required to exactly match. Regardless, a sequence read could have a contiguous sequence of bases that align to the end sequence of the contig, and the remaining bases of the sequence read can be used to extend the contig.

FIG. 1A shows an example of a contig 110 with an end sequence 112 being extended by sequence read 120. However, the task of extending a contig can be more difficult than depicted with FIG. 1A. There may be multiple sequence reads that align sufficiently to the end sequence.

Figure 1B:
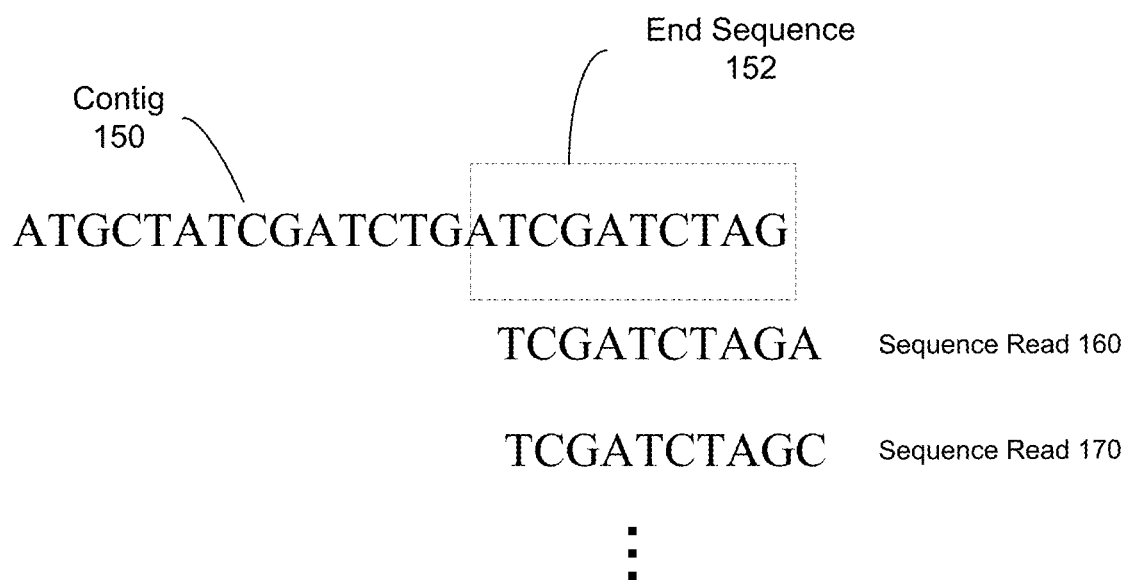
FIG. 1B shows an example where multiple sequence reads (SEQ ID NOS:2 and 3) aligned to the end sequence. Contig 150=SEQ ID NO:1.

FIG. 1B shows an example where multiple sequence reads 160 and 170 aligned to the end sequence 152 of contig 150. If contig 150 is a haploid contig (e.g., corresponding to a particular chromosome), then there is only one correct base that extends the contig. Thus, the correct base must be chosen from among the four bases. In the present case, either of two branches is chosen, namely A or the C is chosen for extension. For a diploid contig, there is at most two branches (options), which is the case when a single nucleotide polymorphism (SNP) is encountered.

The problem can be exacerbated when a contig is extended by more than one base at a time. In such a case, one might possibly have to choose a particular branch from among 16 different branches (e.g., when the number of bases M for extension is 2 bases), depending on which sequence reads aligned to the end sequence of the contig.

Embodiments of the present invention can use various techniques to determine which branch should be chosen for extending a contig.

II. Labels

A label can be used to determine an origin of the nucleic acid molecule (e.g., a long fragment) that the sequence read was obtained. The origin can be a particular nucleic acid molecule; the sequence reads from the same nucleic acid molecule have the same label. As another example, the label can correspond to a particular aliquot (e.g., a well), where each aliquot includes a relatively small percentage of the genome. As explained below, having a relatively small percentage of the genome in an aliquot can allow for an assumption that sequence reads that are similar to each other (e.g., that align to each other) are from a same larger fragment.

A. Example of Labels (Aliquots)

The well that a particular sequence read of a fragment is obtained can be tracked. This well ID can be determined using a barcode that is attached to a small fragment. Thus, the origin of the small fragments can be tracked. The following describes various implementations, which may, for example, be used in embodiments.

Figure 2:
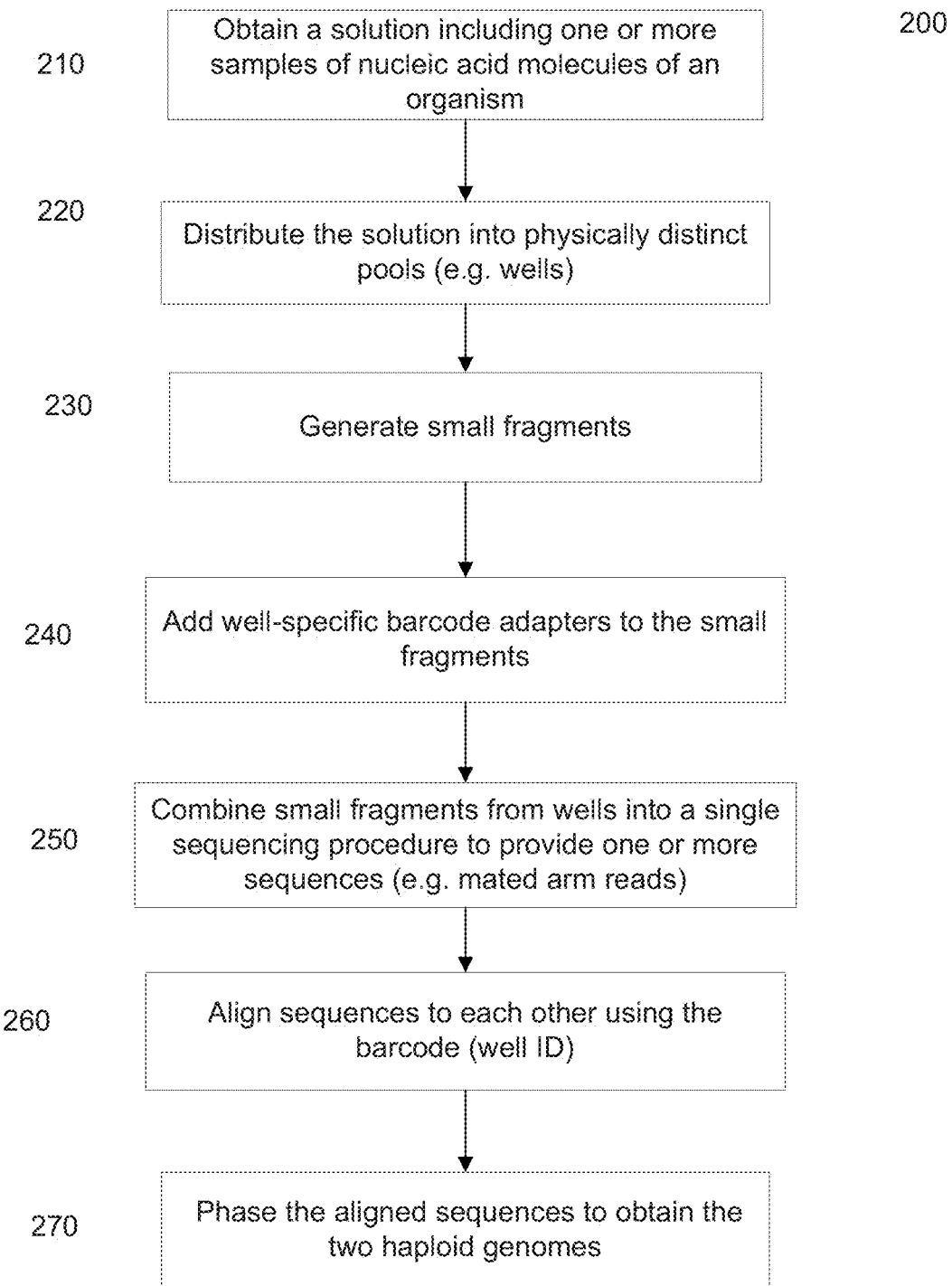
FIG. 2 is a flowchart illustrating a method 200 for obtaining short sequence reads associated with labels of long fragments according to embodiments of the present invention.

FIG. 2 is a flowchart illustrating a method 200 for obtaining short sequence reads for assembling into long fragments according to embodiments of the present invention. Method 200 will be described in conjunction with FIG. 3, which shows a diagram illustrating steps of method 200.

Figure 3:
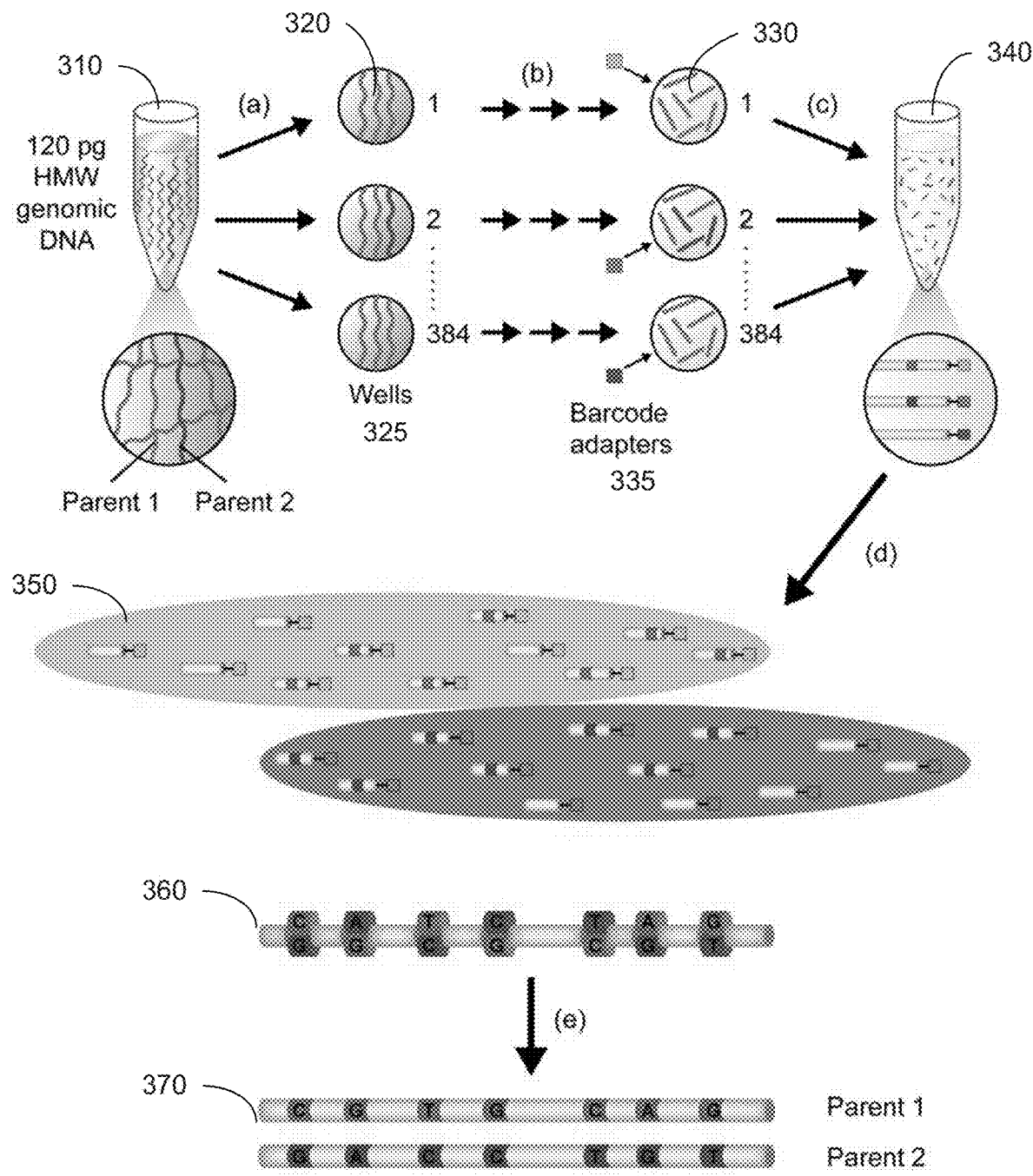
FIG. 3 which shows a diagram illustrating steps of method 200.

In step 210, a solution including one or more samples of nucleic acid molecules of an organism is obtained. Note that a sample can be the solution. The solution can be created from tissue samples, or samples obtained from a bodily fluid. As shown in FIG. 3, sample 310 has approximately 120 pg of high molecular weight DNA. The DNA inherited from each parent is highlighted in blue (parent 1) and red (parent 2). In the solution, the nucleic acid molecules tend to be much longer than after the solution is dispensed (e.g. from a pipette) as an aliquot into wells for preparation for sequencing. These very long fragments in the sample 310 can be about 100 kb to 1 mb in length.

In step 220, the solution is distributed into physically distinct pools (e.g. wells). FIG. 3 shows in (a) the DNA being physically separated into 384 distinct wells 320. The separation can be a stochastic separation of corresponding parental DNA fragments into the physically distinct pools. The act of dispensing typically breaks up the nucleic acid molecules, e.g., as they move through the tip of the pipette. The nucleic acid molecules before dispensing are termed very long fragments, and the nucleic acid molecules after dispensing are termed long fragments. The long fragments in a well (or other container holding a single aliquot) are about 5 Kb to 50 Kb in length (or up to a few 100s of Kb).

In one embodiment, the solution 310 can be relatively diluted with respect to the DNA (e.g. as few as about 10 to 30 cells may be in the solution). This dilution can provide an aliquot containing around 10% of the genome when the solution is dispensed from a pipette. As the fraction of the genome in each pool decreases to less than a haploid genome, the statistical likelihood of having a corresponding fragment from both parental chromosomes in the same pool decreases. For example, at 0.1 genome equivalents per well, there is a 10% chance that two fragments will overlap and a 50% chance those fragments will be derived from separate parental chromosomes; yielding a 5% overall chance that a particular well will be uninformative for a given fragment. Thus, given that the long fragments are randomly distributed throughout the solution, the original fragments of an aliquot are not likely to be from overlapping regions of the genome (nor be close to each other) and to be from different copies of a chromosome.

These long fragments can be amplified (cloned). For example, a highly uniform amplification using a modified phi29-based multiple displacement amplification (MDA) (Dean, F. B. et al. 2002, PNAS Vol. 99, pp. 5261-6) was performed to increase the number of each long fragment of DNA to 5,000-10,000 copies per well. Amplification can help to provide better statistical data for the histograms. The long fragments are not be cloned at all, or may be cloned in later steps.

In step 230, small fragments are generated from the long fragments. FIG. 3. shows the long fragments 325 being broken into small fragments 330 as shown in (b). The long fragments can be fragmented, e.g. using enzymatic fragmentation, multiple displacement amplification (MDA) with random primers, and/or physically fragmented (e.g. using sonic fragmentation). Short fragments result from the fragmentation of the long fragments. As part of an enzymatic process or as an additional step, the resulting short fragments may be amplified. In various embodiments, the resulting short fragments can be about 100-10,000 bases, or a more narrow range of 200 bases to 5,000 bases, and may be 500 bases on average.

As part of the fragmentation into small fragments, the long DNA molecules can be processed to blunt ended 300-1,500 bp fragments through controlled random enzymatic fragmenting (CoRE). CoRE fragments DNA through removal of uridine bases, incorporated at a predefined frequency during MDA, by uracil DNA glycosylase and endonuclease IV. Nick translation from the resulting single-base gaps with E. coli polymerase 1 can resolve the fragments and generate blunt ends.

In step 240, well-specific barcode adapters are added to the small fragments. Thus, the short fragments of a single aliquot can be coded, as described in U.S. patent application Ser. No. 12/816,365, to track the short fragments from a same well, when the short fragments from all wells are pooled into a single sequencing procedure. FIG. 3 shows barcode adapters 335 being added to the small fragments 330. Each well has a barcode that is unique to that well. In one embodiment, unique 10-base error correcting barcode adapters, designed to reduce any bias caused by differences in the sequence and concentration of each barcode, are ligated to the fragmented DNA in each well using a high yield, low chimera formation protocol (Drmanac, R. et al. 2010, Science, Vol. 327, pp. 78-81). In one implementation in step (b), all within the same well without intervening purifications, the genomic DNA is amplified, fragmented, and ligated to unique barcode adapters.

In step 250, the small fragments from the wells are combined into a single sequencing procedure to provide one or more sequences (e.g. mate pair reads). In FIG. 3 at (c), the fragments from all 384 wells are combined into a single vessel 340, with the barcode adapters 335 distinguishing the origin of each small fragment. Any sequencing platform can be used to obtain an entire sequence of a small fragment, one arm read, or a pair of mated reads. In one embodiment, an unsaturated polymerase chain reaction using primers common to the ligated adapters can be employed to generate sufficient template for sequencing (Drmanac, R. et al. 2010, Science, Vol. 327, pp. 78-81). The small fragments can also be purified before the sequencing process begins. Alternatively, one could sequence each well in a separate process, but this can be time consuming.

The more individual pools interrogated the greater number of times a fragment from the maternal and paternal complements will be analyzed in separate pools. For example, a 384 well plate with 0.1 genome equivalents in each well results in a theoretical 19× coverage of both the maternal and paternal alleles.

In step 260, the sequences are mapped (aligned) to each other (e.g., form contigs) using the barcode (i.e. by well ID). FIG. 3 shows group 350 of the sequences obtained from fragments from well 1, while the other group is of sequences obtained from fragments from well 2. As each group corresponds to long fragments that are likely not to be overlapping, the reads can be determined to correspond to the long fragments 320. Accordingly, certain embodiments can track the aliquot (or well) from which a sequenced fragment was obtained, thereby recapturing information about the longer fragments that existed in the solution. This information about the longer fragments can provide more information about the respective chromosomes and help in assembling a contig.

For example, when a low concentration sample is used, if sequence reads from any two fragments in a same aliquot (well) are close in genomic location (as determined from the mapping), it can be assumed that they originated from a same original long fragment in the solution. Thus, the sequence reads do not have to be of a same small fragment, but can be from any two fragments that are from the same aliquot. Such tracking provides more information about large regions on the chromosomes, and can allow for more accurate assembly.

In step 270, the aligned sequences can be phased (e.g. using an unzipping process described below) to obtain the two haploid genomes. Since each long fragment in sub-genome aliquoting such as LFR can represent (with >95% confidence) a haploid genome, such a process can significantly simplify the task of DNA assembly. Ultimately, a high coverage complete sequence of both maternal and paternal chromosomes can be generated. FIG. 3 shows a diploid genome 360 of heterozygous loci that is phased into the two haploid genomes 370 with the help of the knowledge of the labels of the long fragments. Further details about LFR can be found in U.S. patent application Ser. Nos. 12/816,365, 12/329,365, and Ser. No. 12/265,593, U.S. Pat. Nos. 7,906, 285, 7,901,891, and 7,709,197, and U.S. Publications 2011/0033854, 2013/0054151, and 2013/0096841, which are incorporated by reference.

B. Other Example

Another example of a label can be found in U.S. application Ser. No. 14/205,145, entitled "Multiple Tagging Of Individual Long Dna Fragments," where a same label can be affixed to different segments of a same long fragment. If the long fragment is broken up into smaller fragments, each small fragment can include the same label. In other embodiments, different segments of the same long fragment can have a same prefix for the label, but have a different suffix. In this manner, a label can identify two small fragments as originating from the same long fragment. In one embodiment, a different label can be assigned as a tag to each long fragment, which can result in many (e.g., millions or billions) of tags, depending on the number of long fragments.

In another embodiment, the nucleic acids in each aliquot can be sequenced separately. In this manner, all the sequence reads obtained in a particular sequencing operation can be associated with the same label. This label can be assigned to the reads when the reads are stored as a group.

C. Expected Number

In various embodiments, an expected number of wells can be used to determine how to extend a contig. For example, if 20 cells are used, then there should be about 40 fragments that correspond to a genomic location in the human genome (i.e., where the location is the same between both chromosomes). When the fragments are sequenced, this information can be conveyed in the labels, and used in the assembly process. Thus, one may expect about 40 different labels (e.g., +/−10) for reads that align to a contig at a particular position.

An expected number of different labels corresponding to reads that align to a contig can be used in combination with various embodiments. For example, an expected number of labels can be used to determine a seed sequence. As another example, an expected number of labels can be used to determine a next base for extending a contig.

In addition to an expected number of labels, an expected number of reads can also be used. The expected number of sequence reads can be derived from the general genome coverage. For instance, if the coverage is 40× on average, one would expect based on a statistical distribution around 20× to 60× reads for a healthy locus. Genomic coverage (e.g., 40×) relates to the amount of sequencing done at the size of the genome. For human genome, 40× multiplied by $3*10^9$=120 billion bases sequenced.

The genomic coverage can be mandated by the required accuracy and tolerable cost. If the required accuracy is 60× and there are only 10 cells, then that dictates a minimum amount of amplification that is needed. Thus, the amount of amplification can be dictated by the sequencing depth desired and the number of initial cells. The number of coverage after amplification a much higher than that actually performed, e.g., 1000× after amplification but all enough sequencing is performed to achieve 40× coverage.

III. Extension

An assembly process of a contig can be viewed as an iterative process, with each iteration providing an extension of the contig. The assembly process can begin with a seed sequence (described in more detail below) to obtain an extended sequence. The contig that is the extended sequence can be further extended iteratively for a plurality of cycles (e.g. >1000, >10,000, or >100,000) of cycles). A plurality of seed sequences can be used as part of assembling a chromosome or genome. Each seed can be extended in parallel.

A. Alignment with End

As described above for FIGS. 1A and 1B, a seed sequence can be extended in a particular direction by aligning sequence reads to an end sequence of the seed for a particular direction. For example, the right end sequence can be the last N bases at the right end of the seed sequence. And, the left end sequence can be the last N bases at the left end of the seed sequence. The same goes for extending a contig at any stage (cycle) of the assembly process.

The alignment can be done in a variety of ways and with various criteria. For example, the sequence read can be required to have a perfect match in sequence for the part that overlaps with the end sequence. Other embodiments can allow for some mismatch in the overlapping part. Alignment can be done with a k-mer index to provide greater efficiency, as described below.

B. K-Mer Index

FIG. 4A shows an example k-mer index 400, where the k-mer length is 12. The first column shows a list of 12-mers, where the list is sorted with all A's being at the top. This organized structure can allow for quicker access and finding a particular k-mer. The index may have additional metadata for identifying different segments that include different ranges of 12-mer. For example, the metadata may provide a tree structure so that a binary tree search or higher order (e.g., an octree) can be used. One example of ordering for the data structure is alphabetical (i.e., A, C, G, T), but other orderings can be used.

These k-mers can be identified by analyzing sequence reads in retrieving sequences of 12 bases long. If the sequence read is longer than 12 bases, then multiple 12-mers can be obtained from the read. The other columns include an identification of sequence reads that include the k-mer of that row. As a k-mer can appear in multiple reads, there can be enough columns to accommodate the total number of reads that include a particular k-mer. However, the number reads including a particular k-mer will vary.

As shown, the second 12-mer has only two reads that include the 12-mer. The symbol "-" indicates that no data is stored. To reduce storage, sparse matrix storage techniques can be used. The read number can be used to access the entire sequence of the read, if the entire sequence is needed. Embodiments described later can include a memory address for a particular read in the k-mer index. In one aspect, the second 12-mer may not be the next sequential 12-mer (i.e., AAAAAAAAAAAC; SEQ ID NO:14) for various reasons, such as that k-mer does not exist in the sequence reads or due to variations in the organization of the data in the index.

An index may be used in various ways to extend a contig. In one embodiment, the end sequence is taken be the same length as a kmer of the k-mer index. Thus, the end sequence is K bases in length, and the index is made of sequences of K bases. For a given end sequence, the k-mer index can be searched to find a matching sequence. Once the magic sequence is found, the reads that include that matching k-mer can be identified and retrieved. The bases of the retrieved reads can be used in extending the contig. For example, the bases that surround the matching k-mer can be used for the extension. Additionally, bases of a read before the matching k-mer can be used to determine whether the read is in fact a match.

FIG. 4B is a diagram showing a read 420 including a k-mer that matches to the end sequence 412 of contig 410. Read 420 is shown to have two bases before the k-mer and three bases after the k-mer. Once read 420 is retrieved from the kmer index, the bases internal to the contig can be compared to the contig to determine alignment of the entire read. In the example shown, the two internal bases do align to the contig, which provides further evidence that read 420 is properly aligned. The three external bases can be used to extend the contig. Whether only the first external base is used to extend or whether the second and third are used can be determined based on how many other reads are consistent with these external bases. The number of bases used to extend can also be set at a predetermined amount and be the same for each extension cycle.

In another embodiment, the end sequence of the contig has a different length than a k-mers in the index. For example, the end sequence can have a length of nine bases in the index can have k-mers of length 10. The index can be searched for k-mers whose first nine bases match the end sequence. In this example, the searcher be for any of the four 10-mers that might match. Other embodiments can use an index is k-mers that are more than one base longer than the end sequence. For instance, the end sequence can be length K–N, where N is a number of bases for each extension iteration.

FIG. 4C is a diagram showing an end sequence 452 of length 9 (K–1) and two k-mers 460 and 470 of length 10. In this example, both of the k-mers have the first nine bases matching to the end sequence. The two k-mers have different bases in the $10^{th}$ position. The number of reads associated with each k-mer can be used to determine which base (or possibly both) to use for extension. The left side of the contig can be extended in a similar fashion.

If all four of the possible 10-mers are found in the index (or even if there are two or more for haploid contig extension), then the number of reads corresponding to each matching k-mer can be used to determine how to extend. In one implementation, the k-mer having the most reads can be chosen for extending the contig. In another implementations, additional or different criteria can be used, as is described herein. For example, the count of reads can be of those with expected labels, where expected labels may be determined based on a representative set associated with the current contig. Further details are provided below.

C. Branches

When extending there may be different options (branches) for the next base. As explained below, labels can be used to select the best option for the next base; mate pair information can also be used. Besides determining which branch (e.g., next N bases) is correct, embodiments can also determine which reads of a branch are correct.

For example, if the end sequence can be found in many places of the genome (e.g., a repeat sequence), then some of the seemingly matching reads are actually from a different part of the genome. Different parts of the genome with the same sequence correspond to different sub-branches. Issues can arise if the wrong reads are used (this will become evident in a discussion of an external cloud, as provided below). Thus, there can be issues for which mate pairs are correct and which are repeats from other parts of the genome.

1. Het (Branch)

When extending a diploid contig (i.e., there are two chromosomes that have not been identified yet), two branches are possible, each for a different haplotype. Thus, when extending diploid contig, the determination is to be made as to whether two branches are viable. Each branch can correspond to a different base at a particular location. Such a locus can be referred to as the heterozygous locus, or simply "het".

Figure 5A:
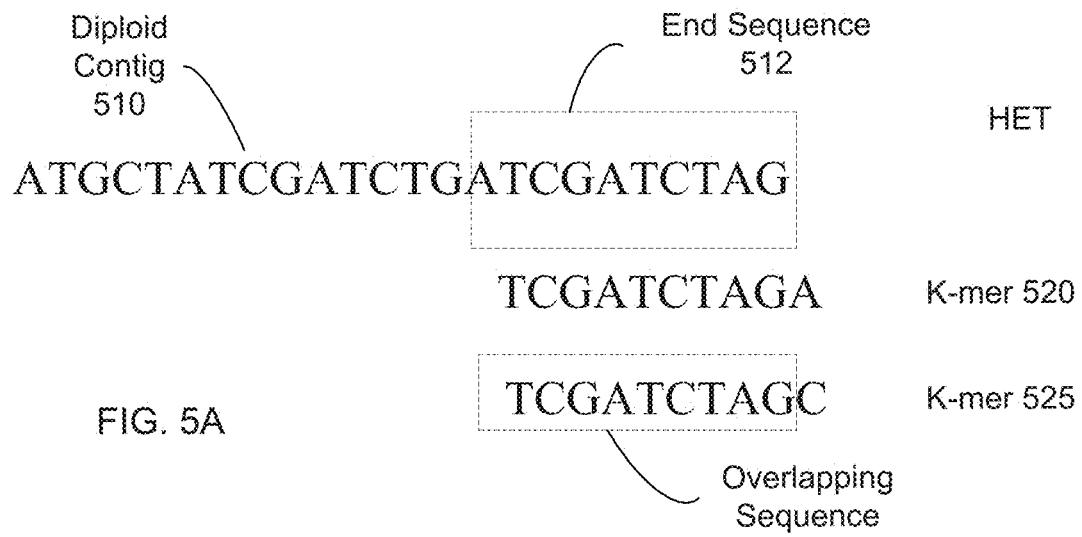
FIG. 5A is a diagram showing two k-mers (SEQ ID NOS:2 and 3) aligning an end sequence of the contig (SEQ ID NO:1).

FIG. 5A is a diagram showing two k-mers 520 and 525 aligning an end sequence 512 of a diploid contig 510. The extended position can correspond to a het. Embodiments can determine whether the different matching k-mers are due to a het, or due to similar sequences in the genome, or possibly even sequencing errors. To make the determination, the number of reads associated with each k-mer can be counted and/or the number of different labels for the associated reads can be counted.

For instance, if 40 cells are in the sample, one would expect about 40 labels for each k-mer branch. Certain acceptable ranges for the number of labels can be used, e.g., 40+/−10. However, if one of the branches as a number of labels is significantly deviates from 40 (e.g., 5) and the other branch is about 80, then just one branch may be chosen. In this manner, the best branch can be chosen, and two branches would not be selected when the data does not support two branches.

As another example, one branch could have about 40 different labels, and the second branch could have significantly more than 40 different labels. In such a scenario, the second branch could be correct, but implicate a sequence that is repeated in the genome. It can also happen that both branches that more than expected number of different labels. And, there can be more than two branches that might seem viable. Such scenarios can be difficult to determine whether both branches are correct, or if only one branch is correct. Further details for selecting a branch are provided below.

Figure 5B:
FIG. 5B shows two haploid contigs (SEQ ID NOS:8 and 9) after a het is encountered and two branches are selected.

FIG. 5B shows two haploid contigs 530 and 535 after a het is encountered and two branches are selected. The process of creating two haploid contigs from a single diploid contig is referred to as unzipping. The diploid contig represents a sequence that is common to both haplotypes. When a difference between the two haplotypes (e.g., the het as shown) is encountered, the resulting two haploid contigs can be extended independently. Embodiments can identify different labels for the different haploid contigs, as will be described below.

In some embodiments, a number of exclusive wells with each branch can be determined, and the number of exclusive wells for each branch can be used to determine whether a locus is truly heterozygous or the reads with the other allele are due to sequencing errors. An exclusive well is one that includes evidence of only one branch, e.g., only one allele. For example, assume that there are ten reads with A and three reads with G, this data may not be conclusive as to whether a locus is heterozygous.

In such a situation, the number of wells that exclusively have one or more reads with G and the number of wells that exclusively have one or more reads with A can be determined. The number of exclusive wells can then be used to determine whether the locus is heterozygous. For example, if the number of exclusive wells with G is 9 and the number of exclusive wells with A is 1, then the locus can be called as being homozygous. In one implementation, the number of exclusive wells can be required to be more than a threshold number of exclusive wells (e.g., where the threshold is between 3 and 10). Other criteria can be used in addition or instead of such a threshold number of exclusive wells. For example, the ratio of exclusive wells (e.g., higher number divided by smaller number) can be required to be less than a specified number, e.g., less than 5.

2. Repeats (Sub-Branches)

As mentioned above, there can be more reads corresponding to a particular branch than is expected. For example, for a haploid contig where the sample has 40 cells, one would expect 40 different labels for the correct branch. However, it can be significantly more than 40 labels. For example, there can be 120 different labels, which suggests that there are three parts of the haploid genome that have the same sequence as the current contig. Each of the similar parts of the genome correspond to different sub-branches. One can know that the one branch is correct (e.g., the next base), but one does not know which reads (sub-branch) actually correspond to the current contig.

Figure 5C:
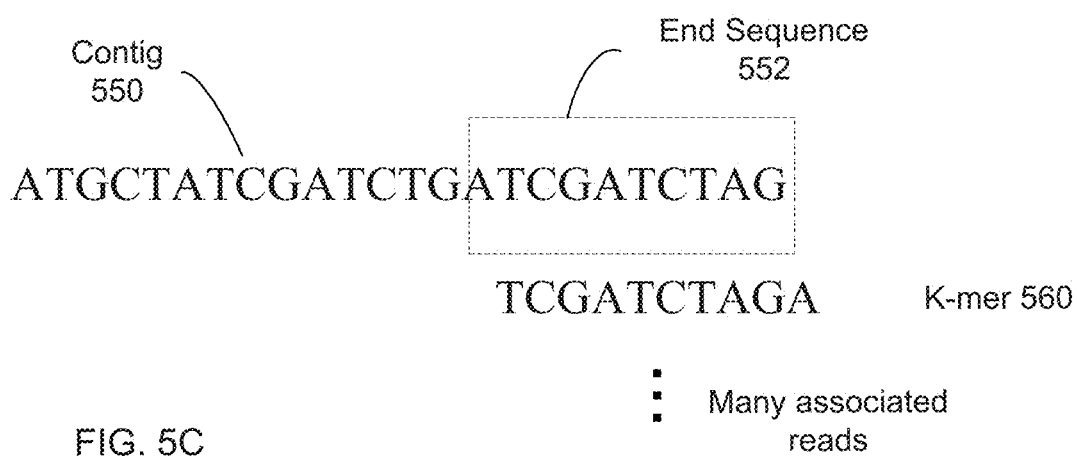
FIG. 5C is a diagram showing one k-mer (SEQ ID NO:2) aligning an end sequence of the contig (SEA ID NO:1).

FIG. 5C is a diagram showing one k-mer 560 aligning to an end sequence 552 of the contig 550. Although there is only a single k-mer, the number of associated reads is significantly more than expected. Thus, an assumption can be made that there are multiple sub-branches that each result from a repeat part of the genome. There can be many branches for repeats, each corresponding to a different part of the genome, where the fragment actually came from. As is described below, embodiments can identify the reads corresponding to the correct sub-branch, i.e., the reads corresponding to fragments that correspond to the current (ative) contig.

D. Using Overlapping Reads in Extension

When extending a contig using reads that overlap with an end of the contig (which may involve using kmers), the number of reads may be small. For example, two kmers may overlap, and only one or two reads may be associated with each overlapping kmer. Thus, there is not much evidence of which branch to choose, or even enough confidence to choose a branch, even if it is the only option. This could cause the extension of the contig to stop, which is undesirable.

To address this problem, some embodiments can proceed to find other kmers/reads that overlap with the initial overlapped reads. Thus, the overlapping with the contig may not be sufficient per initial criteria, but the matching the initial overlapping reads can be sufficient. In this manner, the number of reads at the next position for extension can be increased, thereby providing the desired accuracy (e.g., a minimum number of reads at a position for extension).

Figure 5D:
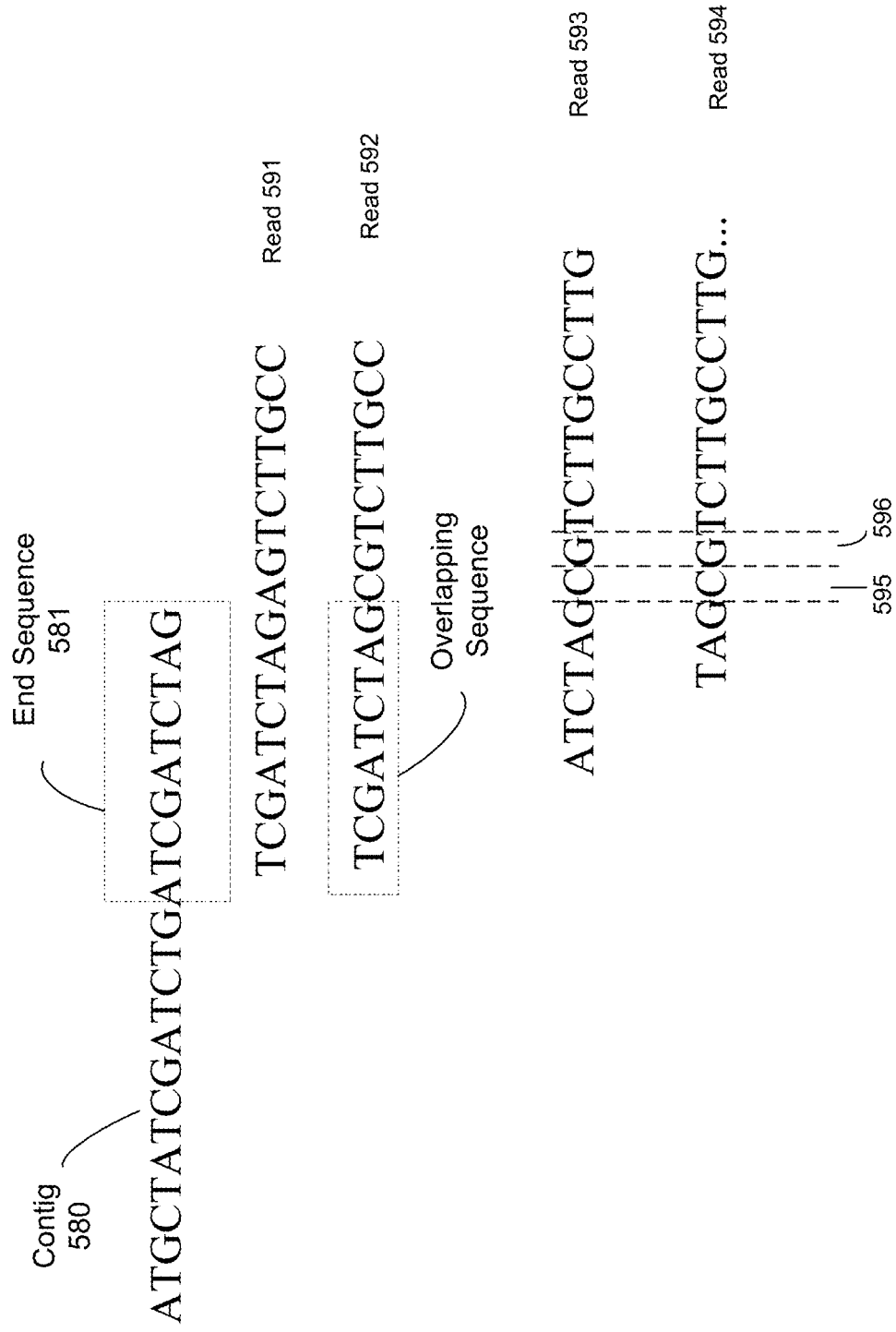
FIG. 5D is a diagram showing the use of aligning reads (SEQ ID NOS:10-13) to overlapping reads to obtain more reads for extension according to embodiments of the present invention. Contig 580=SEQ ID NO:1.

FIG. 5D is a diagram showing the use of aligning reads to overlapping reads to obtain more reads for extension according to embodiments of the present invention. Contig 580 is being extended. Reads are aligned to end sequence 581. The length of contig 580 and end sequence 581 are used for illustration, and the lengths can be more or less. For example, end sequence 581 can be between 5-40 bases.

In this example, read 591 and read 592 sufficiently align to end sequence 581, e.g., by aligning to 9 bases. But, these are the only two reads that align to 9 bases. Thus, with only two reads, there is not enough information for extension. Further, in this example, read 591 and read 592 have a different base in the next position for extension. Thus, read 591 can be one hypothesis (branch) and read 593 can be another hypothesis (branch).

To obtain more information for extending, embodiment can align other reads to the hypothesis sequences of read 591 and 592. The alignment can use kmers, and then the full read for the aligning kmer can be retrieved. In FIG. 5D, reads 593 and 594 are shown aligned to initial overlapping reads 591 and 592. As a result, there is more evidence that the next base for extension 595 is C and not A.

In one embodiment, a process of aligning reads to the initial overlapping reads can be performed until a threshold number of reads are obtained for a next extension position. The number of initial overlapping reads can vary, and the threshold can be predetermined or dynamic. The threshold can be applied to each branch, or just to the total number of reads for a given extension position.

Each extension position can be checked to ensure that there is a sufficient number of reads overlapping with that extension position. Thus, if more than one extension position has a sufficient number of reads (e.g., at least a threshold number of reads for a given branch), then the contig can be extended by all of the extension positions that satisfy the criteria. For example, if enough reads align to extension position 596 with G at position 596, contig 580 can be extended by two bases. Thus, the number of bases for extension can be limited by the significance of the coverage, which can be stopped once the threshold coverage is obtained for the next extension position, which is 595 in FIG. 5D.

IV. Seed Sequence

The assembly process begins with a seed sequence. Ideally, the seed sequence is a unique sequence in a genome. If the seed sequence is unique, embodiments can be guaranteed to map the reads to the right place (assuming no errors in the reads, and that the genome of interest matches the genome reference for that sequence). If the seed sequence was not unique, the particular assembly would build a contig for multiple parts of the genome simultaneously, and errors may arise from using an incorrect read for extending a contig.

A seed can be selected in various ways. For example, a seed can be selected from the reference genome. As another example, a seed can be selected based on the reads, e.g., reads of the genome that have k-mers that appear once in the genome. A seed can be the size of the k-mers in the index being used. With a unique k-mer, one can aligned reads to the right place by simply identifying all the reads that have that k-mer.

The length of the seed can be selected to provide a higher degree of certainty as to uniqueness. Example lengths include 16-29 bases. There are some times that 20-base sequence that is unique, even though there are some non-unique 20-base sequences. For every base added to a seed sequence, the result is four times higher likelihood of uniqueness. However, the length of the seed and the k-mer index is balanced with read errors. For each additional base, the total probability of an error in any one of the bases increases. A determination can be made about what read error rate is tolerable, and thus determine the longest k-mer that is acceptable.

A. Using Reference Sequence

In some embodiments, it can be useful to use a reference sequence (which may be all or part of reference genome) to identify a unique sequence. The k-mers in an index determined from the reads may often not be unique. One way to use a reference is to find out which k-mers are supposed to be unique in the reference. For example, one can take a k-mer from the index and compare it to the reference to determine whether the k-mer appears in more than one location. Although such an embodiment uses a reference to determine a seed, the reference is still only used in a minimal sense.

B. Using Expected Labels

Instead of or in addition to using the reference, an expected number of labels for a k-mer can be used. The expected number of labels corresponding to a k-mer can be used as a proxy for determining that it is unique within the genome. The expected number of labels can be determined or estimated, as described herein. For example, the number of cells in the sample can be used to determine the expected number of labels.

If there are 20 cells, you may expect 40 labels as a result. Thus, if the number of labels for the k-mer is around 40, plus/minus 10 (or other suitable range), then you can say it is a valid seed. If there are 200 labels (i.e., 200 reads with different labels, where the reads include the k-mer), then the k-mer can be identified as not a valid seed. As the creation of fragments and the selection of reads is a stochastic process, embodiments might consider a range of 10-80 to be suitable when 40 labels are expected.

In one embodiment, the seed sequence can be selected as follows. The number of effective labels (i.e., the number of labels after clones have been removed) may be specified to be in a certain range, e.g., (1+/−epsilon)*2*number of cells or cell equivalents, where epsilon defines the acceptable tolerance. The algorithm can define a series of initial k-mer seeds. Each seed can then be operated on in parallel.

The use of a reference sequence and the use of an expected number of labels can be used in combination. For example, k-mers having a number of labels within an acceptable range can be identified. These identified k-mers can be compared to the reference to determine whether or not the k-mers are unique within the reference.

C. Polymorphic Seeds (Two Haploid Seeds)

The assembly process can start from a seed that is unique, but not unique between the two chromosomes. Such a process would start from a diploid seed. Other embodiments can use a seed that is unique to a particular haplotype, with such a seed corresponding to a haploid seed. Using haploid seeds, the assembly process starts with a haploid contig, instead of having to separate out two haploid contigs from a diploid contig during the assembly process.

For example, two haploid seeds can correspond to a polymorphism in the genome. In one implementation, the polymorphism can be identified from a database, such as dbSNP. A certain a database can be specific to a particular population (e.g., to select a polymorphism that occurs often for particular population). Once a polymorphism at a particular position in the genome has been identified, the sequence reads (e.g., via an index) can be searched to verify that the polymorphism exists in the reads for that position in the genome. For example, if each of the two alleles is found in at least a threshold number of non-exclusive or exclusive wells (e.g., any value between 2-5).

Once a locus has been verified as being polymorphic in the sample, two haploid seeds can be created for that locus. The reads that correspond to one allele of the polymorphism would be used to create one haploid seed and the reads that correspond to the other allele of the polymorphism would be used to create the other haploid seed.

In one implementation, the wells corresponding to a particular allele of a polymorphic locus can be used to create the seed. These wells can be identified as corresponding to a particular haplotype, e.g., when that well appears in only the wells associated with one allele for the polymorphic locus. Thus, even if a read does not align to the polymorphic locus (e.g., as determined by mapping to a reference), embodiments can use the well ID (or other label) to know that another read is from the same long fragment as the read that maps to the polymorphic locus, even though the other read does not a map to the polymorphic locus. For example, the wells that have an A at a particular locus can identified, and these wells can be used to create the haploid seed the vicinity of the locus (i.e., for the haplotype with A at the particular locus).

In some embodiments, more than one polymorphic locus can be used (e.g., between 2-10). For example, two alleles (e.g., SNPs) of two polymorphic loci that are close to each other may be known to commonly occur on a same haplotype. Thus, the reads (e.g., both arms of a mate pair) corresponding to these two alleles can be used to determine the haploid seed, which would then cover both polymorphic loci. In this manner, the haploid seed can be larger than if only one polymorphic locus is used.

If two polymorphic loci are relatively near to each other (e.g., within a few tens of thousands of bases) then the fragments that align to the two loci can be from the same long fragment and thus from the same set of wells. It may be possible to start a haploid seed at each polymorphic locus, and join the separate initial haploid seeds into a larger haploid seed. Thus, depending on how close the polymorphic loci are, two haploid seeds that correspond to the same haplotype can be created and then joined by extending one or both of the haploid seeds. Such operation can proceed in a similar manner as using a helper contig, as described herein.

Using multiple polymorphic sites allows determining more accurately the list of labels corresponding to each parent (haplotype) at the given genomic locations without connecting seed sequences between polymorphic sites (e.g., labels that are associated with at least two alleles from two polymorphic sites out of 5-10 such neighboring sites). This would reduce false positive and false negative results in defining labels for each haplotype (parent) at the given genomic location. Having such label lists allows building haploid seeds starting from any unique sequence (unique k-mer) in the given genomic location that includes one of the polymorphic sites, with the building using reads from the defined corresponding labels. Once the seed is long enough (e.g. 50-70% of the average mate-pair length), mate-pair information can be used in addition to label information to extend the seed into a longer sequence contig bridging repeats longer than the read and shorter than most of mate-pairs.

If there are repeat regions between the two seeds, then it may be more difficult to join the seeds. Mate pair information can be used to help span a repeat region, e.g., using a local kmer index, as described herein. For example, if one seed is not large enough to start using mate pair information, another seed at another polymorphic locus can be used (e.g., a locus that is near the one seed). In one implementation, one read of a mate pair can extend an initial seed created using the other read of the mate pair. The one read of the mate pair can correspond to a repeat region. If the two haploid seeds correspond to alleles that are known to commonly occur on the same haplotype, then the two haploid seeds can be joined.

One benefit of using haploid seeds is that there is only one branch for extension, whereas two branches could occur for a diploid see. Of course, after those two branches are taken to create haploid contigs, then only one branch would occur for each haploid contig. But, starting with haploid contigs avoids having to make a decision about when two branches do occur. And, when the polymorphic locus is identified from a database and there is evidence of polymorphism in the reads, then there is a higher likelihood of identifying the two branches, resulting in the two haploid seeds.

Figure 17:
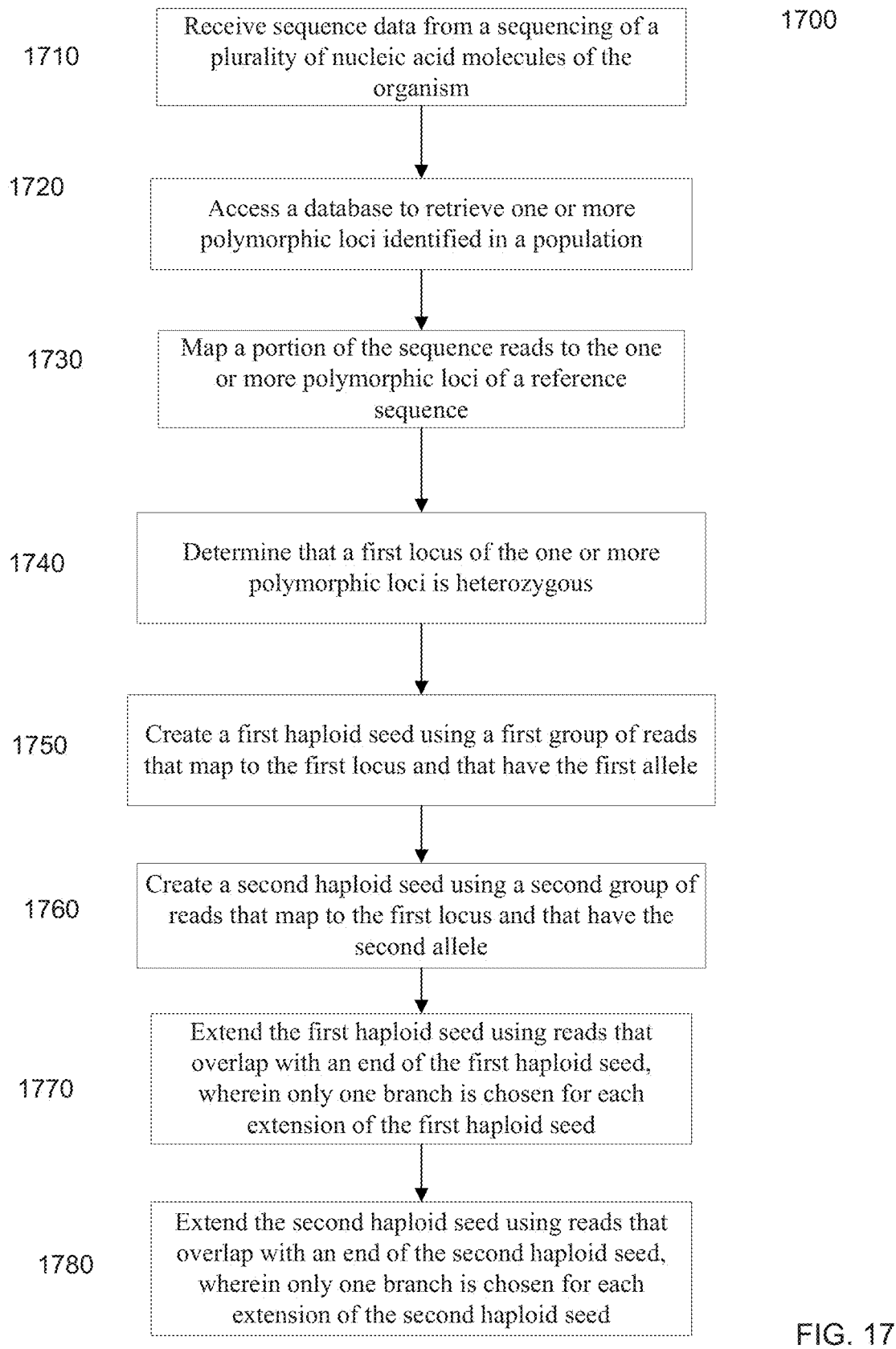
FIG. 17 is a flowchart of a method of creating haploid seeds for assembling a sequence of a first chromosomal region of an organism according to embodiments of the present invention

FIG. 17 is a flowchart of a method 1700 of creating haploid seeds for assembling a sequence of a first chromosomal region of an organism according to embodiments of the present invention.

At block 1710, a computer system receives sequence data from a sequencing of a plurality of nucleic acid molecules of the organism. The sequence data for each of the plurality of nucleic acid molecule includes one or more sequence reads of at least one portion of the nucleic acid molecule. Block 1710 can be performed as described herein.

At block 1720, a database is accessed to retrieve one or more polymorphic loci identified in a population. For example, dbSNP can be used to identify such polymorphic loci.

At block 1730, a portion of the sequence reads are mapped to the one or more polymorphic loci of a reference sequence. This may be done by checking the presence of a segment of the reference sequence (including a polymorphic locus) in the reads from the given sample. Or, the presence of a sequence read can be found in the reference sequence at a polymorphic locus. As the polymorphic loci are identified, the mapping can be to specific parts of the reference sequence. In this manner, specific parts of the organism's genome can be tested, where those specific parts are known to likely be heterozygous. Thus, this process can be more efficient than analyzing the reads alone to identify hets.

In one example, using a reference sequence, a k-mer is defined for each allele for each known polymorphic site. Using such k-mers and k-mer index for the reads of the given sample, the presence of these polymorphic sites is checked in the given sample. Other reference defined k-mers, especially that occur once in the reference, can be used for defining more seeds for growing contigs or helper contigs especially for difficult repeats.

At block 1740, it is determining that a first locus of the one or more polymorphic loci is heterozygous. The reads mapped to the first locus indicate an existence of a first allele and a second allele at the first locus in the first chromosomal region. For example, a certain number of reads can have the first allele and a certain number of reads can have the second allele. Other techniques using labels (e.g., exclusive labels) can be used to determine that the first locus is heterozygous. For example, if both alleles from a known polymorphic site have enough reads from enough distinct labels in the given sample, the considered site can be identified as polymorphic in that sample.

At block 1750, a first haploid seed is created using a first group of reads that map to the first locus and that have the first allele. For example, the first allele can be A, and the first group of reads can have A at the position of the first locus. The creation of the first haploid seed can also include extensions as described in later blocks.

At block 1760, a second haploid seed is created using a second group of reads that map to the first locus and that have the second allele. For example, the second allele can be G, and the second group of reads can have G at the position of the first locus. The creation of the second haploid seed can also include extensions as described in later blocks.

At block 1770, the first haploid seed is extended using reads that overlap with an end of the first haploid seed. The extension can be performed using techniques described herein, e.g., using a representative set of labels that correspond to reads used to create the first haploid seed. Only one branch is chosen for each extension of the first haploid seed. Thus, the extension can be more efficient and/or accurate as branch detection is not needed.

At block 1780, the second haploid seed is extended using reads that overlap with an end of the second haploid seed. The extension can be performed using techniques described herein. Only one branch is chosen for each extension of the second haploid seed.

V. Using Labels for Extension

As described above, labels can be used to determine how to extend a contig. The labels provide information about how many fragments of the sample include a particular sequence. For example, 20 cells should provide 40 long fragments for particular chromosomal region for human. If an expected number of fragments is known, a comparison between the number of labels having reads that align to the contig and the expected number can be used. As another example, reads having labels that are the same as reads previously aligned to the contig can be used.

A. Expected Number of Labels

As mentioned above, the number of reads corresponding to a particular branch may be used in determining whether or not to use that branch. For example, if the first k−1 bases of the k-mer aligns to the last k−1 bases of the end sequence, the number of reads that include the k-mer can be used in determining whether or not to use the k-mer and extending the contig. The same analysis also follows when surrounding bases (i.e., base is next to the k-mer in the read) are used in determining how to extend.

The reads corresponding to a particular branch can be analyzed to determine the number of different labels. It is possible that two reads could have the same label; this might occur when two reads are clones of each other or when amplification results in two reads with a same label covering the same part of the genome. The number of labels can be used as a guide as to the number of fragments that correspond to the branch. If the number of labels is very low relative to an expected amount (e.g., five where expected number is 40), then the branch might be discarded, potentially as resulting from sequencing errors or an insignificant level of somatic mutation. If the number of labels is within a specified tolerance of an expected number, then the branch can be identified as being viable. Depending on the number of viable branches, for the analysis may be needed. If the number of labels is high relative to an expected amount (e.g., 200 where expected number is 40), then the branch can be identified as having sub-branches that need to be resolved. The resulting of sub-branches is described in more detail below.

Accordingly, a contig can be extended by: determining an expected range for a number of labels of sequence reads corresponding to a correct branch for extending the first contig; and selecting, for extending the first contig, sequence reads of the first group that correspond to a first branch having a number of labels within the expected range as the correct branch.

B. Representative Set of Labels for a Contig

A contig can have a representative set of labels, e.g., a representative set of wells from which reads are prioritized for extending the contig. Representative set of labels can be created in various ways using various criteria. The representative set can be used in resolving branches and sub-branches by identifying reads that are likely part of the contig. Reads that have the same labels are likely from a same contig, and thus one can use reads having the same labels as has already been used in creating the contig.

FIG. 6A shows an example for how a representative set of labels may be created for a seed sequence. As shown, the seed sequence corresponds to a k-mer in an index, where the k-mer corresponds to a unique part of the genome. As described above, the k-mer can be identified based on various factors, including the number reads including the unique k-mer. The reads that include the unique k-mer can be identified from the index, and the labels for these reads can be identified (e.g., by the index storing a label associated with the corresponding read).

FIG. 6A shows four reads that include the k-mer that is the seed. The number reads would typically be higher, but for shown for illustrative purposes. Each read is depicted that the corresponding label above it. These labels can comprise the representative set to start extension of the seed. The reads that have the same labels are likely to correspond to the part genome that is adjacent to the seed. For example, reads that are in well 45 are more likely to be from the same long fragment that includes read 610, than reads from the wells that are not in the representative set. As a reminder, in an embodiment where a label corresponds to a well that receives a long fragment, the reads can be determined from small fragments obtained by fragmenting the long fragment. Thus, the other small fragments result from fragmenting the one long fragment would have the same label, and these small fragments should be the ones used to extend the seed to obtain the same sequence as the long fragment.

Although the creation of the contig will re-create a long fragment of a single well, embodiments use reads from multiple wells to form the representative set, thereby providing an accurate contig. Thus, the contig can be assembled to determine a correct sequence using information obtained from multiple long fragments.

FIG. 6B shows an example for how a representative set of labels may be updated and maintained for contig. Assuming that the contig 650 is created from the seed 605, the contig is shown as a result of a plurality of extension steps. Reads are shown at locations where the read was used to extend the contig. Thus, the representative set can be determined based on the labels of reads that are used to extend the contig. Although each extension step may use reads from multiple wells, the reads are shown with a single label for illustrative purposes.

As shown, the labels from FIG. 6A also appear in reads that are used to extend the contig. Labels can be added to the representative set when reads having a label used in extending the contig. For example, once reads that overlap with the end sequence, one knows the corresponding labels associated with the overlapping reads. These corresponding labels can be added to the representative set. In one implementation, an overlapping read may be identified from a match of a k-mer index.

The representative set of labels can also be referred to as neighborhood labels (or neighborhood wells). The use of neighborhood can convey that the wells are within the reach of a long fragment (e.g., less than a length of the long fragment). The reads from these neighborhood wells are most likely to be the reads degenerating to the current contig.

C. Extending Using Representative Set

The representative set may be used in various ways to extend a contig. One embodiment can determine the base(s) for the extension step only using reads having labels from the representative set. Another embodiment can use reads with labels that are not in a representative set, but use the representative set to determine which branch to take.

1. Using Labels Only from Representative Set

In one embodiment, one can only use reads within the representative set to determine which base(s) are to be added to the contig for the extension step. In this manner, the universe of possible reads used to extend the contig is reduced, thereby making the extension process more efficient. Also, as an amount of reads being analyzed for the extension step is reduced, a likelihood of using incorrect reads may be reduced.

The creation of the representative set allows one to identify reads that are consistent with the current contig, by focusing on reads having a label from the representative set. The use of consistent reads can reduce the chance of using reads from other parts of the genome that have a similar sequence to the contig.

At some point the representative set can be updated, which may occur at each step or after a specified number of extension steps. Thus, only reads having a label within the representative set is used to determine what base is used to extend the contig, but other reads that are consistent with the extension can be identified and their labels may be added to the representative set. This can allow for instances where the contig reaches a new long fragment (e.g., when a contig gets too long), which would have reads with the new label.

2. % of Representative Set

In some embodiments, one can consider all reads when determining which base(s) are to be added to the contig for the extension step. The representative set can still be use though. The branch for extension can be selected based on which branch has reads with labels that are most similar to the representative set.

Each branch can have its own set of labels that are associated with the reads consistent with the branch. For instance, if the branch corresponds to adding an A to the contig, the reads consistent with adding the A can be identified. The labels of these identified reads can also be determined. These labels correspond to a branch set of labels.

To determine whether a branch is a viable option, the labels of the brand set can be compared to labels of the representative set of the contig. The number of labels that are the same within each set can be determined. The larger the number of shared labels, it can be viewed that the branch is more consistent with the current contig. The number of expected reads of a branch can also be used in combination with the number of shared labels. For example, criteria can be that the number of reads should be between R1 and R2, and the number of wells should be between W1 and W2.

To select a branch, various criteria can be used if the spectrum number of shared labels. The number of shared labels can be required to be greater than an absolute threshold and/or a certain percentage of the reads associated with the branch. An absolute threshold can depend upon the size of the sample (e.g., a number of cells), and thus depend upon an expected number of labels for a branch. For percentage, a minimum percentage for the shared labels compared to the total labels for branch can depend based on whether the contig is diploid or haploid.

Besides using thresholds that are required, the same values (e.g., absolute number of shared labels the percentage of shared labels) can be used as criteria when determining a particular branch to choose. For example, the branch with the highest number of shared labels can always be chosen. As another example, the branch with the highest percentage of shared labels can always be chosen (e.g., 90% of the reads of the first branch have shared labels and the other branch has only 30% of the reads with shared labels).

Further, if two branches have similar values for the shared labels, the algorithm can proceed to use other criteria in selecting a branch, e.g., using a reference or a table of genetic variants known to occur. For example, the branch that corresponds to the reference can be selected. The table of genetic variants can include a frequency of occurrence for each genetic variant (e.g., SNVs). The frequency can be broken out into a frequency for different populations of the organisms (e.g., different populations based on race, ethnicity, or national origin for humans). For the genetic variants, if one branch corresponds to a known genetic variant (which may be required to be from the same population as the current organism being tested), then that branch can be selected, e.g., in instances where other techniques do not fully resolve which branch to select.

D. Updating Representative Set

From time to time, the representative set can be updated to add labels or to remove labels. For example, assume that a contig had a first representative set of labels. As reads are added to extend the contig, the contig can extend to each new long fragment, which can have different labels (e.g., be in different wells). Thus, new labels can be added when such reads are used to extend the contig (note that such reads include reads that are simply consistent with the extension, as opposed to strictly using these reads to determine which branch to select, e.g., as is described above for using only reads with labels of the representative set to select a branch).

If the contig becomes very long, the ends of the contig may extend past a long fragment from a particular well. In this case, the label for that well can be removed. Various criteria can be used to determine when to remove a label from representative set. For instance, a distance criteria may be used for when all last week with a particular label was used or was consistent with extension step. For example, if a read with a label corresponding to well 56 was last used 1000 bases (or steps) ago, then the label 56 can be removed from the representative set.

The removal of labels for the representative set is a type of retirement, and the criteria used can be referred to as a retirement schedule. Other types of retirement (e.g., with respect to mate pairs) is discussed below. In some embodiments, retirement may not be used, e.g., when the length of the contig is not sufficiently long. In one implementation, retirement may only be started once the contig is larger than a threshold length.

The representative set can be updated at each step or at every N extension steps. In addition and removal of labels can be done at different intervals. For example, multiple extension steps may be performed to choose the branch for each step, while the reads and corresponding labels used for the extension or consistent with the extension can be saved the last N steps. After that step, the representative set can be updated using the saved reads and labels.

For removal, each label in the representative set can have a corresponding counter that determines the last step that involved a read having a label. When a new read having a label is used in an extension step, the counter can be set or reset, as the case may be. If the counter exceeds a threshold, the label can be removed from the set. For example, the representative set can be composed of labels only for those reads that have been used for the last M bases (e.g., last 1000 bases). If seed is 100 kb, then not have a retirement would cause too many labels, and thus the representative set of labels would no longer be representative of the end of the contig. As a contig can be extended in either direction, both directions can have a different set of labels.

E. Method Using Labels

FIG. 7 shows a method 700 for assembling a sequence of a first chromosomal region of an organism using labels according to embodiments of the present invention. For method 700 and other methods described herein, molecules generated by in vitro amplification can be treated as molecules of the organism. Method 700 can be performed entirely or partially by a computer system, as can other methods described herein.

At block 710, sequence data is received from a sequencing of a plurality of nucleic acid molecules of the organism. The nucleic acid molecules can correspond to small fragments as described herein. The sequencing of a nucleic acid molecule may be performed using any suitable sequencing technique. The sequence data for each of the plurality of nucleic acid molecule can include one or more sequence reads of at least one portion of the nucleic acid molecule. For example, the sequence data can include mated reads of a mate pair, or just be a single sequence read.

The sequence data can also include a label corresponding to the one or more sequence reads. A single label can correspond to all the sequence reads for a given molecule. As a label can be stored for each sequence read, or distort once for all reads of a given nucleic acid molecule. As described above, the label indicates an origin of the nucleic acid molecule, e.g., the origin being a well or specific long fragment which the molecule originated.

At block 720, a first contig of the first chromosomal region is received. The first contig can be a seed sequence or any extended sequence resulting from an extension step. As examples, the first contig can be received from external source, the retrieved from memory, or determined internally by a computer system performing an assembly process.

At block 730, the first contig is extended using a group of sequence reads that overlap with an end sequence of the first contig. In one embodiment, the group of sequence reads can be determined using a k-mer index. The group of sequence reads can include sequence reads with a plurality of different labels indicating different origins. For example, sequence reads from a plurality of different wells can be used to determine how to extend the first contig. Examples of how such information by reads from multiple wells is described elsewhere in this application.

VI. Unzipping/Haplotypes

A diploid contig (DC or DipCon) is a contig for which the phases of the two haplotypes are unknown. For example, a seed sequence can correspond to a part of the genome they shared between the two chromosomes of a diploid organism. As the seed sequence appears in both haplotypes, the seed sequence can be considered to represent both haplotypes. Until a sequence variation between the two haplotypes is encountered, the contig can be extended as a diploid contig the represents both haplotypes.

At some point, two branches can be identified as being valid, where each branch corresponds to one of the haplotypes. For instance, a het can be identified, e.g., where two branches are equally represented (e.g., both have similar number of reads, # of wells, same labels as representative set). After encountering the split of the two branches, two different sequences result. These two different sequences, corresponding to a different haplotypes, can be referred to as haploid contigs.

The process of separating a diploid contig into two haploid contigs is referred to as unzipping. In one embodiment, the unzipping can occur at the first variation encountered, and the assembly process for the first haploid contig can proceed independently from the assembly process of the second haploid contig. The assembly process for the first haploid contig contractor representative set of labels for the first haploid contig, the second haploid contig can have its own representative set of labels for extension.

In another embodiment, the unzipping can occur after the extension of the contig is stopped (e.g., when an accurate extension is not identified). Thus, the assembly process can continue with the whole contig as diploid, where the locations of the polymorphic sites are tracked. Once the contig is established as complete (e.g., no more extension possible), and unzipping process can proceed to determine the specific sequence for each haplotype, using the stored locations and assignments (i.e., which allele corresponds to which haplotype) for the polymorphic sites. When a possible polymorphic site is encountered, a representative set for each haplotype can be used to determine a valid branch for each haplotype.

As an example, when a seed is started, the location in the genome is not known. By just random chance (e.g., if the seed is short—20 bases), the seed would typically not include a polymorphism, although a seed could be selected to include a polymorphism, e.g., using candidates from dbSNP. As the contig is grown, the contig would hit a variation (e.g., a SNP or indel)—SNPs are about 1 in a 1,000 bases and indels are about 1 in 10,000 bases). After a certain number of polymorphisms (e.g., just one or a specified number), the unzipping can identify labels are specific to one haplotype, which can be useful in extending the haploid contig correctly and efficiently. For example, after unzipping, the number of labels of the representative set might be reduced in half.

A. Method of Unzipping

Figure 8:
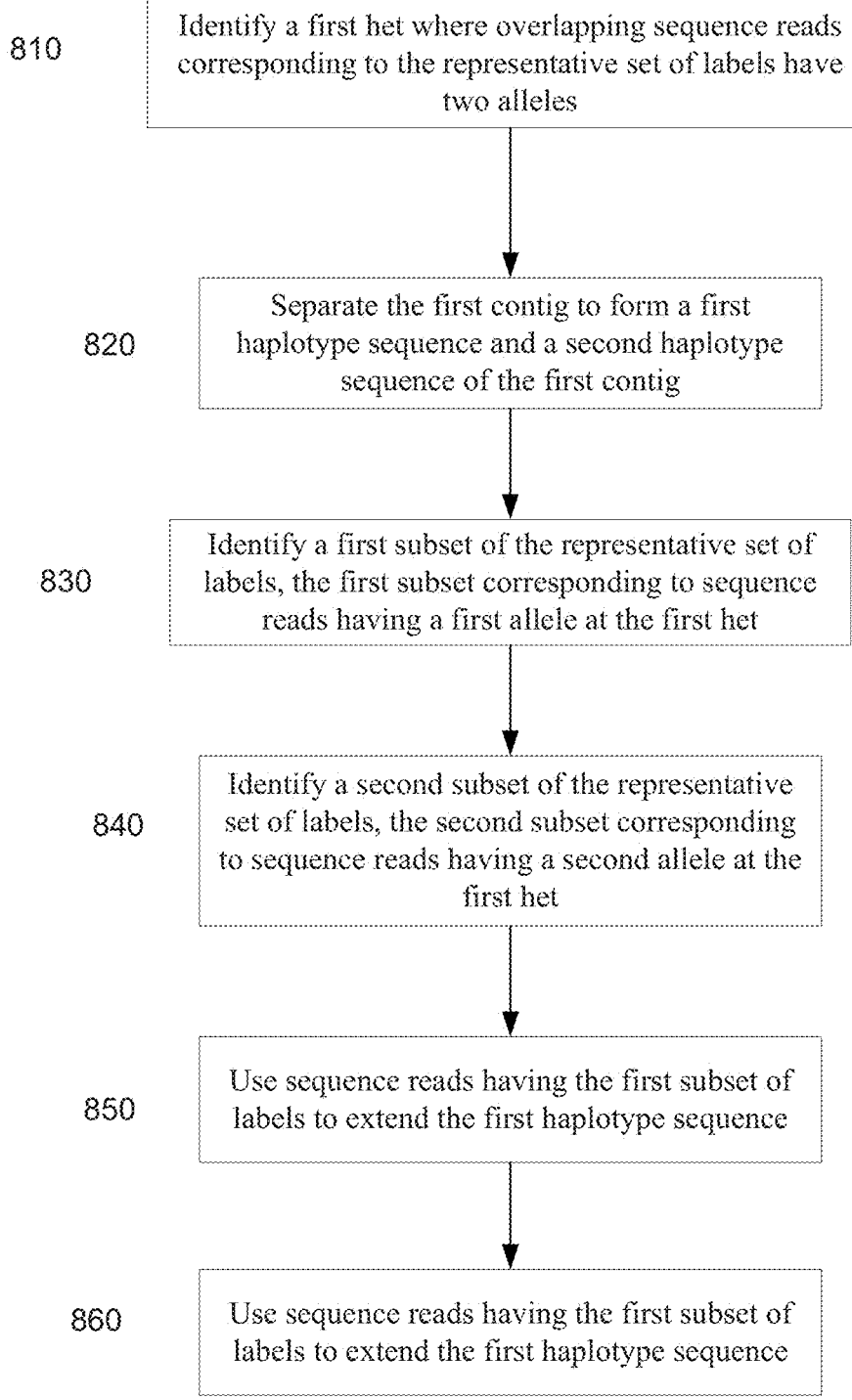
FIG. 8 shows a method for determining and extending haploid contigs according to embodiments of the present invention.

FIG. 8 shows a method 800 for determining and extending haploid contigs according to embodiments of the present invention.

At block 810, a first het is identified where overlapping sequence reads corresponding to the representative set of labels have two alleles. The overlapping sequence reads can be of similar number for both branches, thereby suggesting a het. Other techniques for identifying a het are described herein.

At block 820, the first contig is separated to form a first haplotype sequence and a second haplotype sequence of the first contig. A first haplotype sequence corresponds to a first haploid contig, and the second haplotype sequence corresponds to a second haploid contig. The separation may occur at a point of assigning one allele to the first haploid contig and the other allele to the second haploid contig.

At block 830, a first subset of the representative set of labels is identified. The first subset corresponds to sequence reads having a first allele at the first het. This first subset corresponds to the labels that are representative of the first haploid contig.

At block 840, a second subset of the representative set of labels is identified. The second subset corresponds to sequence reads having a second allele at the first het. The second subset corresponds to the labels that are representative of the second haploid contig.

At block 850, sequence reads having the first subset of labels are used to extend the first haplotype sequence. In one embodiment, the extension may occur at the next base after the first contig is separated into the two haploid contigs. In another embodiment, the extension may be at a second het, which may occur many bases after the first het. The labels of the first subset may be used in a similar fashion for the extension, as described elsewhere in this application.

At block 860, sequence reads having the second subset of labels are used to extend the second haplotype sequence. This extension can occur in a similar manner as the extension of the first haplotype sequence (haploid contig). In the extension of a haploid contig, no further unzipping would occur.

B. Unzipping with Indels vs. SNPs

An insertion or deletion (indel) is another polymorphism and can exist between two haplotypes. An indel can be any number of nucleotides, as opposed to the single nucleotide of a SNP. As an indel can be larger, it can be easier to identify an indel has opposed to a SNP, as there is more resolution for deciding if the two haplotypes versus one haplotype. With this larger divergence, using different representative set of labels to extend each haploid contig independently can be advantageous, since the two haplotypes differ significantly. The ability to handle indels with a consistent methodology can provide higher accuracy, as opposed to mapping-based techniques, which use special algorithms to handle indels.

Once an indel is found on one haplotype, the extension of the haploid contigs can occur independently. In another embodiment, a point where the two haploid contigs begin again to share bases can be identified. For example, after a deletion and when the next base is the same in both haploid contigs, a joint extension process can be used that uses all the sequence reads for extending both haploid contigs.

C. Extending Haploid Contig

In one embodiment, the two haploid contigs can be extended independently. For instance, when a het is encountered, a flag may be set to indicate method contig is a haploid contig. This flag may be used in determining that only one branch can be valid for extending the haploid contig. It can happen that one haploid contig can be extended, while the other haploid contig hits a region through which an extension is not clear (e.g., one haploid contig may have a repeat region).

Even if the extension of a second haploid contig is stopped at one location, the extension of that haploid contig can be restarted. For example, if the extension of the first haploid contig continues, the extension can encounter two branches, where the branches show an equal number of reads and/or labels. Such an occurrence can indicate the existence that one of the branches corresponds to the second haploid contig. At this point, the extension of the second haploid contig can resume. For the part of the genome where the extension of the second haploid contig was paused, an indication can be stored that this part of the second haploid contig is unknown.

D. De-Zipped Contig

A genome can have large regions where the two haplotypes are identical, i.e., no heterozygotes are found. If such regions are large enough (e.g., around 100 Kilobases, then phasing information is lost. For example, the representative set of labels for both haploid contigs can converge to a combined set of labels. In such a situation, it can be difficult to identify when a heterozygote does occur. In one embodiment, the number of exclusive labels may be used, e.g., as described above regarding branches.

In an example where one lone heterozygous locus (het) is identified in a region that is otherwise identical between the two haplotypes, phasing information is not available when other heterozygous loci (hets) is too far way. For instance, the next closest het may not share any of the same labels as the lone het. In this case, a genotype at the lone het can still be identified, e.g., using the number of exclusive labels.

VII. Mate Pairs and Clouds

Besides or in addition to labels, mate pairs can be used in an assembly process. Mate pairs are two reads of different parts of a fragment so that the two reads at most partially overlap (beginning and end of one read respectively occur after beginning and the other read), and typically have a separation distance (mate gap) between the end of one read in the beginning of the other read. Example mate gaps are between 100-1,000 bases (e.g., with an average of about 600 bases) or 500-5,000 bases (e.g., with an average of about 1,200 bases). Examples of a mate pair include two reads at either end of a fragment, one read had one and the other read at a middle portion of the pregnant, and two reads both in a middle portion of the fragment.

A general cloud/index (also referred to as a read k-mer index (RKI)) corresponds to any mate pairs having reads that may align to the end sequence of a contig. In various embodiments described below, the general cloud may be searched to find sequence reads that align to the end of the contig. In other embodiments, an external cloud (index) and/or internal cloud (index) may be used to search for reads that align to the end of the contig, or be used to confirm which branch or sub-branch is correct. The use of the internal cloud and external cloud can be particularly useful when the end sequence of a contig reaches a repeat region of the genome. The length of the k-mers in RKI can be different than the length of the k-mers in the internal and external indexes, i.e., different values of k for the different indexes.

A. Mate Pairs

Figure 9A:
FIG. 9A shows a diagram of a mate pair. The two solid lines indicate the two reads of the mate pair.

FIG. 9A shows a diagram of a mate pair 910. The two solid lines indicate the two reads of the mate pair. The dotted line represents the mate gap between the two reads. Nucleic acid molecules have a particular orientation so that when one sequences a fragment one can determine which of the two reads is first (given the particular orientation) and which the two reads is second. Thus, for collection of mate pairs, one can identify a first set of first arm reads and a second set of second arm reads. A single fragment can have more than two reads, and thus there can be more than one mate pair for a given fragment.

As both reads of the mate pair are known to come from the same fragment, the alignment of one read indicates that the other read is in the neighborhood of the end of the contig. For example, if the first read (left read as depicted) is aligned to the right end sequence (i.e., for extending contig to the right), the second read should be within a certain number of bases (as defined by the mate gap) of the end sequence. In a slightly different example, if the second read (right read as depicted) is aligned to the right end sequence, then the first read may align to the contig (e.g., the first read may have been used in previous extension step) if the contig is longer than the mate gap.

Figure 9B:
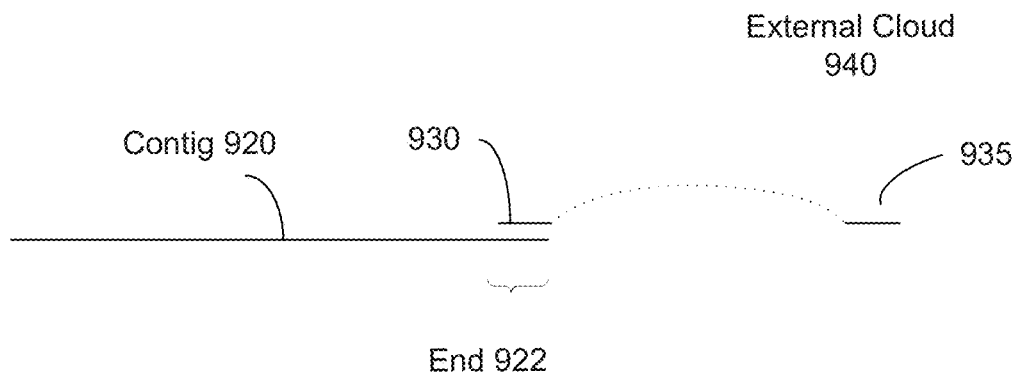
FIG. 9B shows an example of a first read (left read) of a mate pair that aligns to an end of the contig.

FIG. 9B shows an example of a first read 930 (left read) of a mate pair that aligns to an end 922 of the contig 920. The second read 935 is shown as an undetermined location further to the right of the contig 920. This step may be done when the contig 920 is being extended to the right. Although the exact location of the second read 935 is not known, its existence within some neighborhood of the end 922 of the contig 920 can be used to resolve branches and sub-branches, as is described below. Specifically, the second read 935 in this situation can be added to an external cloud 940 to provide some information about the future parts of the contig that likely would be encountered in future extension steps (e.g., any of the next M extension steps, where M is proportional to the mate gap).

Figure 9C:
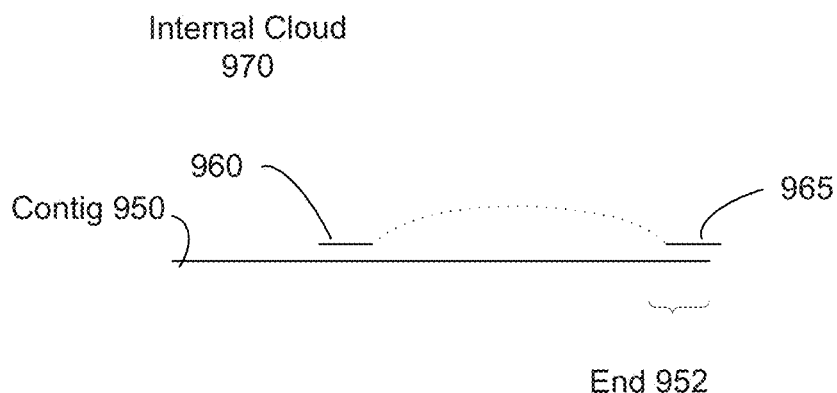
FIG. 9C shows an example of a second read (right read) of a mate pair that aligns to the end of the contig.

FIG. 9C shows an example of a second read 965 (right read) of a mate pair that aligns to the end 952 of the contig 950. The first read 960 is shown at a location internal to the contig 950, which in this case is to the left of the right end of the contig. In this example, the alignment of the first read 950 to the contig 950 increases the likelihood that the second read 965 does indeed correspond the end sequence 952 of the contig 950. First read 960 can be added to an internal cloud 970. In various embodiments of an internal cloud, an alignment can be specifically done for the first read to the internal parts of the contig, or an internal k-mer index can be used as a proxy for the alignment of the entire first read.

In various embodiments, the mate pairs can be useful when two or more branches are viable after the label analysis. Mate pair can also be used to confirm when there is only one viable branch, to ensure no errors. Mate pairs can also be useful when repeat regions are encountered. For example, if a contig has a length of length 1,000 bases or more, and a 20-mer index is use for extending the contig into a repeat region, the number of reads corresponding to the matching 20-mer can be very large (e.g., into the thousands when the expected number is only 40-80). The mate pairs can help resolve these sub-branches they correspond to reads from other parts of the genome, which just happened to be similar to the repetitive nature of the genome.

B. Internal Cloud

As discussed above, embodiments can use the alignment of a first read to an internal part of the contig in the process of determining whether or not the corresponding second read of the mate pair aligns with an end of the contig. An internal cloud can simply refer to determined sequence of the contig that is not part of the end of the contig, but is internal. Embodiments can also create the internal cloud as an internal index of k-mers that align to the internal part of the contig, e.g., have been used to extend the contig.

1. Creation

In one embodiment, the internal cloud can be created or identified by the sequence of a certain part of the contig. For example, internal cloud can be the sequence of the contig is a specified distance away from the ends of the contig. In one implementation, the specified distance can depend on an expected, average, or minimum mate gap distance between the two reads of the mate pair. For instance, if the minimum mate is 100 bases, then the internal cloud can be a sequence of the contig, with the 100 bases on each end excluded.

In other embodiments, the internal cloud can be created as a collection of sequence reads that have aligned to the contig. In one embodiment, k-mers of these aligned sequence reads can be identified and added to an internal k-mer index. The internal k-mer index can be searched to find any k-mers of a given first read (or details are provided below).

In some embodiments, a left internal cloud and right internal cloud can be created. For example, if the contig is very large (i.e., much larger than the mate gap), then a separate left internal cloud and right internal cloud can be created and maintained. The left internal cloud can correspond to the part of the contig that is at least a specified distance (e.g., minimum mate gap) from the left end of the contig, but less than a specified distance (e.g., maximum mate gap) from the left end of the contig. The right internal cloud can be similarly defined.

Figure 10A:
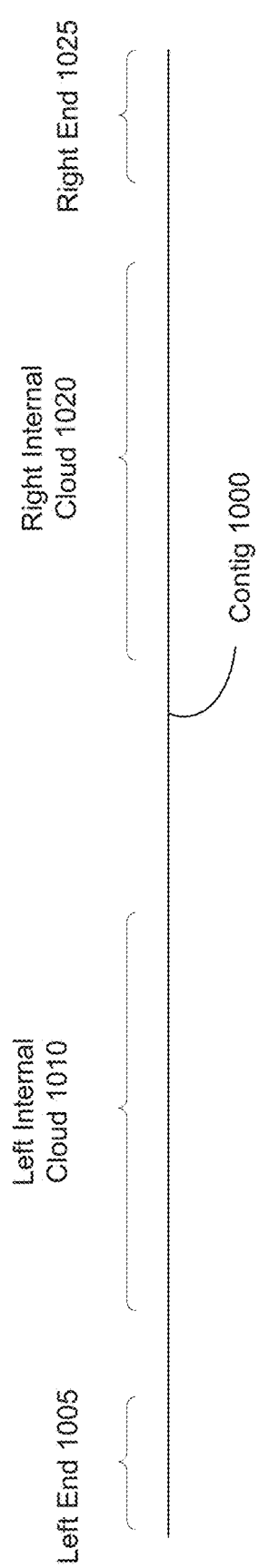
FIG. 10A shows an example contig with a left internal cloud and right internal cloud identified according to embodiments of the present invention.

FIG. 10A shows an example contig 1000 with a left internal cloud 1010 and right internal cloud 1020 identified according to embodiments of the present invention. The depicted internal clouds can be represented by the actual sequence within the range specified. In another embodiment, the specified range corresponds to which k-mers are stored in the index. If a k-mer was used and extension step that falls outside the range, the k-mer can be removed (also called retired). The internal cloud can also include the end of the contig.

2. Using Internal Cloud to Select Second Arm Reads for Extension

The internal cloud can be used to identify second reads to be used in extending the contig, as the first reads are consistent with the internal cloud. For example, when the second read aligns to the end sequence, the corresponding first read can be compared to the internal cloud. If the first read aligns to the internal cloud (e.g., a k-mer the first read is found in the internal k-mer index), then the second read can be identified as being a viable branch.

In one embodiment, second arm reads of the general cloud can be compared to the end sequence to identify a group of sequence reads that align to the end sequence, but the first group may include two branches. That is, a first subset of the group can correspond to sequence reads that would extend the contig with an A, and a second subset of the group can correspond to sequence reads that would extend the contig with a G.

Figure 11A:
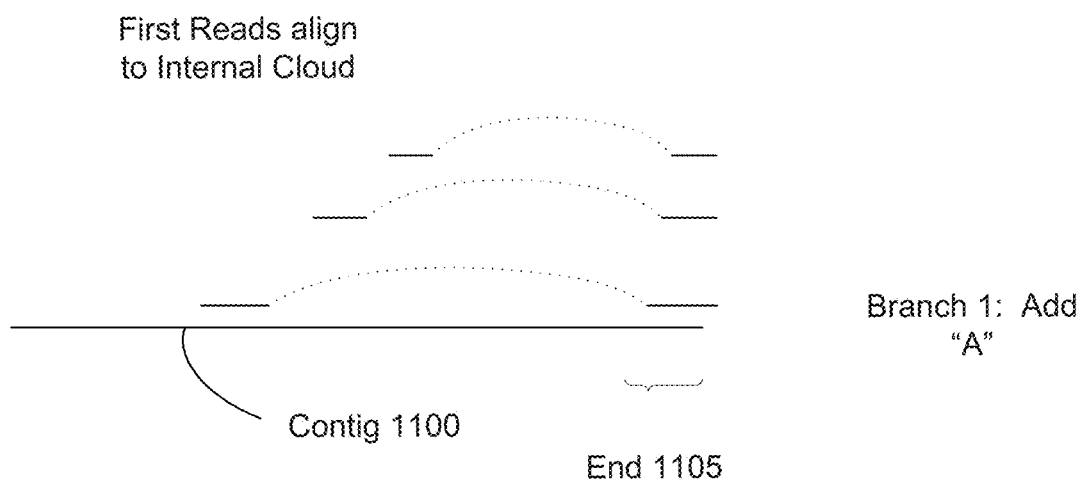
FIG. 11A shows a diagram of the contig with the second read of a branch 1 that aligns to the end of the contig.

FIG. 11A shows a diagram of the contig 1100 with the second reads of a branch 1 that aligns to the end 1105 of the contig 1100. As depicted, the corresponding first reads of the mate pairs align to the internal cloud. The second reads have a sequence that would extend the contig with an A. Multiple second reads are shown as aligning to the end of the contig with support of branch 1 to extend the contig with an A. If all or a substantial portion of the reads of branch 1 aligned to the internal cloud, this is good support that branch 1 is a viable branch. As stated above, the alignment to the internal cloud can use k-mers.

Figure 11B:
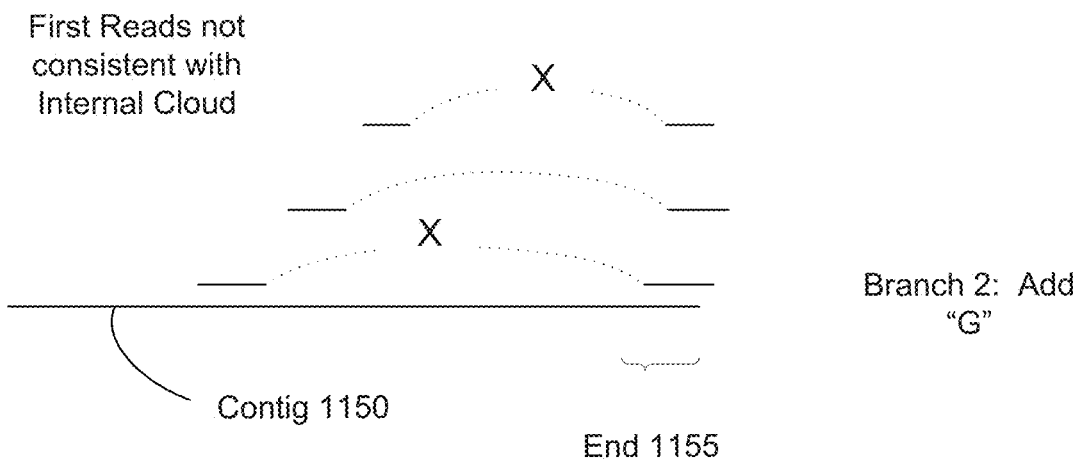
FIG. 11B is a diagram of the contig with the second read of a branch to that aligns to the end of the contig.

FIG. 11B is a diagram of the contig 1150 with the second read of a branch to that aligns to the end 11555 of the contig 1150. As depicted, the corresponding first reads of the mate pairs generally do not align to the internal cloud. As shown, two out of the three first reads do not align to the internal cloud. When compared to the alignment quality of branch 1, this indicates that branch 1 is more likely to be the correct branch. Such a determination can be made in combination with the analysis of the number of labels for the reads of each branch, and the total number of reads for each branch. The same analysis can be used to select between sub-branches.

Accordingly, the corresponding first arm reads of a first branch can be compared to the internal cloud to determine how consistent these first reads are with the internal cloud (the comparison can simply be to the sequence of the contig, as an internal cloud may just be the initial sequence). The corresponding first reads of a second branch can also be compared to the internal cloud. Scores can be determined for each comparison and the branch that is most consistent with the internal cloud can be selected for extending the contig.

When the alignment to the internal cloud uses a k-mer index, the corresponding first reads can each be decomposed into a plurality of k-mers. These k-mers can then be used to search the internal k-mer index. Once a match is found in the internal k-mer index, surrounding bases of the first read can be compared to the surrounding bases within the internal cloud. This may be accomplished by the internal k-mer index identifying a location of the k-mer within the contig. In this manner, the alignment can be more accurate.

Additionally, once the second read is used, the mate pair can be removed from the general cloud, so that the mate pair is not used again and different part of the genome. The k-mers are used, the retirement can occur by removing a particular read being associated with a k-mer, e.g., in the k-mer is used to extend the contig. The above description can also be applied to extending a left end of the contig, but the first and second arm reads would swap.

3. Retirement

As shown in FIG. 10A, the left internal cloud 1010 or right internal cloud 1020 can correspond to a specific part of the contig 1000. This can increase efficiency as alignment need only be made to part of the contig. Further, accidental alignments (e.g., as a result of similarities from different parts of the genome) can be minimized since the internal cloud is kept smaller. The determination of when a sequence read is added to the internal cloud and when it is removed from the internal cloud can be set as predetermined values based on an expected or measured mate gap.

C. External Cloud

The discussion above focused on similarities between a read of a mate pair and the determine sequence of a contig. Embodiments can also use similarities between a read of a mate pair and expected sequences to be encountered extension steps that occur in the near future. If a first read does indeed correspond to an end of the contig, the second arm reads of first arm reads should correspond to the sequences that are expected in the upcoming extension steps. An external cloud can be composed of sequence reads of k-mers from the sequence reads.

Figure 10B:
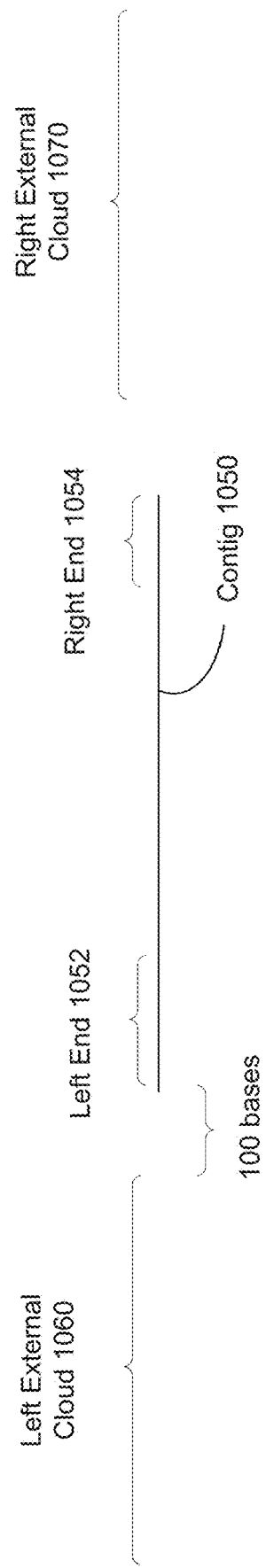
FIG. 10B is a diagram illustrating an external cloud according to embodiments of the present invention.

FIG. 10B is a diagram illustrating an external cloud according to embodiments of the present invention. A contig 1050 has a left end 1052 and right end 1054. External cloud corresponds to sequence reads that are estimated to be a certain distance away from an end of the contig. A left external cloud 1060 is shown to the left of the left end 1052 of the contig 1050. Left external cloud 1060 is shown as having a range of 100 bases from the left edge (very end) of the contig to 2000 bases from the left edge of the contig. This distance can be based on an expected distance of a mate gap. According to the example shown, first reads can be maintained in the left external cloud 1060 for 1,900 extension steps, each extension being one base at a time. The right external cloud 1070 is similar, except that it would include second reads corresponding to first reads used to extend the right end 1054 of the contig 1050.

1. Creation

Figure 12:
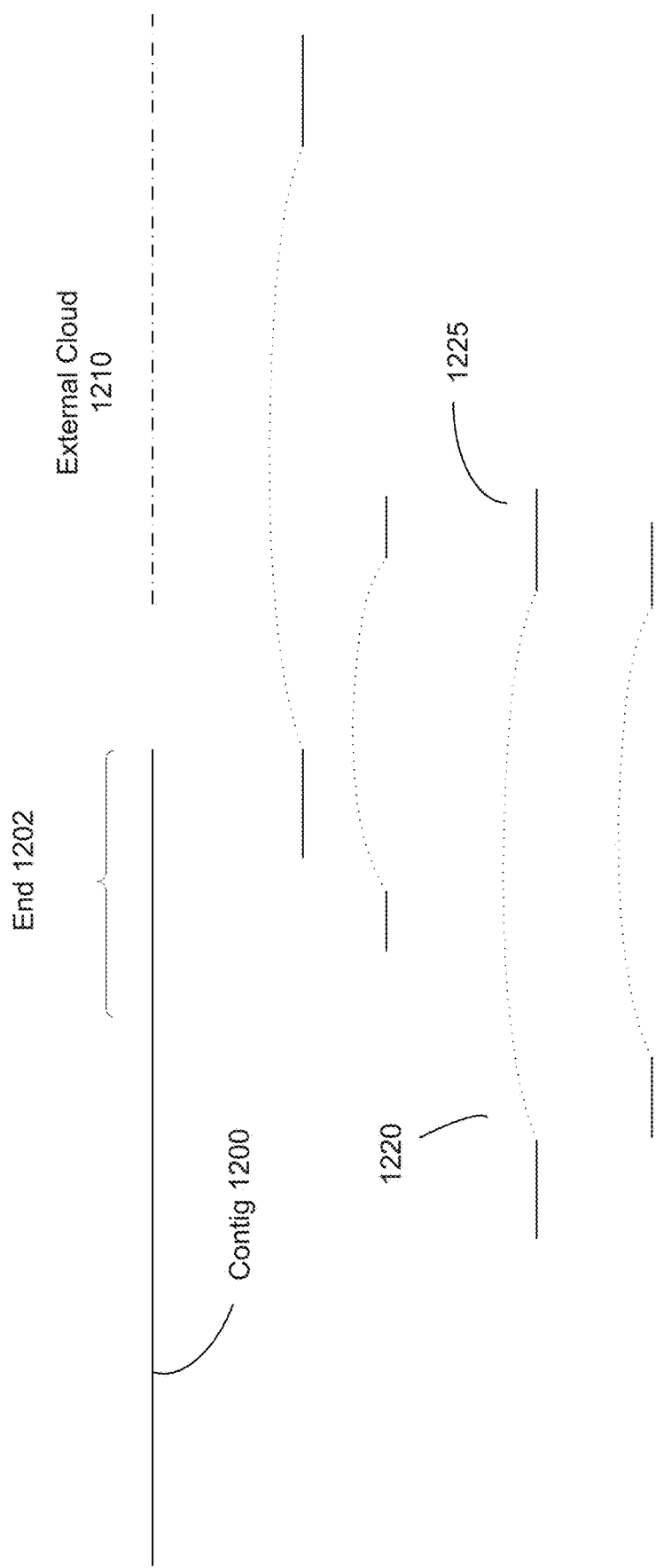
FIG. 12 is a diagram showing the creation of an external cloud.

FIG. 12 is a diagram showing the creation of an external cloud 1210. A contig 1200 is shown at the end sequence 1202 of the contig highlighted. The external cloud 1210 is shown to the right of the right edge of the contig 1200. A group of mate pairs are shown. The first read 1220 of each mate pair is shown at a location that was used to extend the contig. As shown, the second reads 1225 are located at some position within the external cloud.

When a reference sequence is not used, one does not know the mate distance. However, the range of values for the mate gap are known. Thus, even though the exact position the second reads is not known, it can still be determined that the second read will fall somewhere within the external cloud. Thus, the external cloud can provide some representation of the genome, even though the representation is not an exact sequence. As long as a new second read matches to another second read already added to the external cloud, the can be determined that the new second read will likely align to the contig in the contig is extended out to the region currently defined by the external cloud. The first read corresponding to the new second read can also then be confirmed to align to the end of the contig.

Thus, an external cloud can be built with second reads corresponding to the first reads that aligned to the end sequence of the contig. The number of reads added to the external cloud for any given step can be made to confirm with an expected number (e.g., based on number of cells). For example, if the expected number is 40, and there are a first reads that align to the end of the contig, the 40 best matching second reads can be used.

In this manner, the external cloud gives a rough idea about the next 1000 or so bases (depending on mate gap) of the contig. One can use the knowledge of what is coming up to determine which is the correct branch or sub-branch to select. For example, many first reads may align to an end sequence, where some of such first reads actually correspond to a different part of the genome. In such a case, the external cloud can be used to filter out these first reads that do not belong by determining which of the corresponding second reads are consistent with the external cloud.

The external cloud can be represented as an external k-mer index. Both an external k-mer index an internal k-mer index can be composed of different length k-mers, which also may be of a different length than that used to extend the contig. For example, a 20-mer index may be used to identify alignment to the end sequence. A length of 20 may be chosen to provide greater uniqueness throughout the whole genome. But, as internal and external clouds can a much smaller than the whole genome, a lower level of uniqueness can be used. Thus, the internal cloud may use a 10-mer index, and external cloud can use a 10-mer index or even an 8-mer or 12-mer index.

In one embodiment, a second read can be determined as aligning or otherwise consistent with the external cloud when a k-mer from the second read matches with a k-mer in the external index.

2. Using External Cloud to Select First Arm Reads for Extension

As mentioned above, the external cloud can be used to determine which branch or sub-branch of first reads to select when extending the contig. For the correct branch or sub-branch, the second reads should be matching to some second reads of those first reads that are already used. The correct branch should have more overlap with the second reads of the external cloud.

Figure 13A:
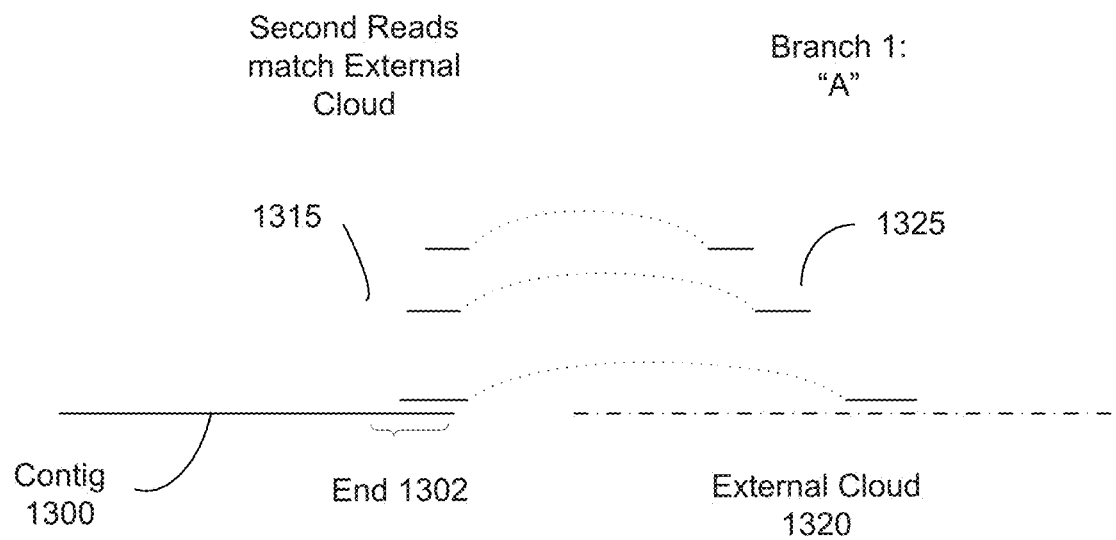
FIG. 13A shows a diagram for the comparison of second reads of first reads of a branch 1 for determining whether to select branch 1 according to embodiments of the present invention.

FIG. 13A shows a diagram for the comparison of second reads 1325 of first reads 1315 of a branch 1 for determining whether to select branch 1 according to embodiments of the present invention. The right end 1302 of the contig 1300 is shown for a process of extending the contig 1300 to the right. A first group of first reads 1315 are shown aligning to the end 1302 of the contig 1300. The corresponding second reads 1325 are shown matching to the external cloud 1320.

Figure 13B:
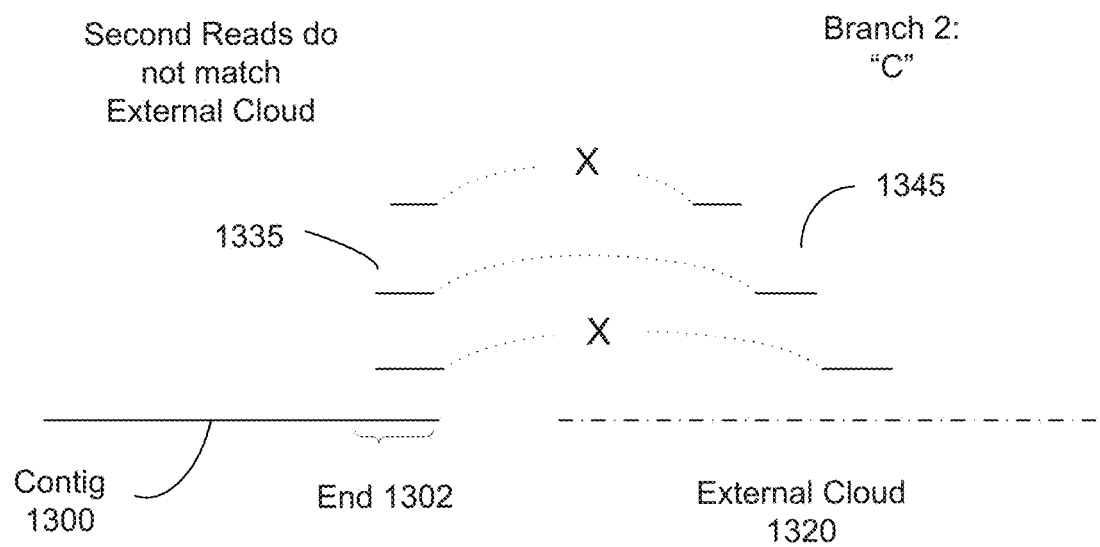
FIG. 13B shows a diagram for the comparison of second reads the first reads of a branch 2 for determining whether to select branch 2.

FIG. 13B shows a diagram for the comparison of second reads 1345 the first reads 1335 of a branch 2 for determining whether to select branch 2. A second group of first reads 1335 are shown aligning to the end 1302 of the contig 1300. But, only one of the corresponding second reads 1345 finds a match in the external cloud 1320. Thus, in this example, branch 1 would be chosen since the second reads 1325 of the first group are more consistent with the external cloud 1320 than the second reads 1345 of branch 2. Note that this example assumes that only one branch is correct, e.g., which may be the case when a haploid contig is being extended. If a diploid contig is being extended (thus allowing for a het to occur), then two branches may be chosen if both of them are equally consistent, and any other branches show less consistency. The level of consistency may be measured as an absolute number or percentage of second reads that have a k-mer matching with the external k-mer index.

Accordingly, the first reads can be compared to the end sequence to determine a first group that aligns to the end sequence. In this first group, there can be first reads that support more than one branch. For instance, there can be first reads that indicate that the next base is an A (first subgroup) that corresponds to a first branch, and there can be first arm reads indicate in the next base is a C (second subgroup) that corresponds to a second branch. Corresponding second arm reads of the first group can be used to determine which branch should be selected for extending the initial sequence.

The second reads of the correct branch should be more consistent with the external cloud, as the second reads should align to the second reads recently added to the external cloud (the external cloud may be kept relatively small to only correspond to second reads that are recently added, e.g., as shown in FIG. 10B).

Second reads can be considered qualified when they match to the external cloud. One may not know the exact location of the sequence read in a genome, other soft support for the sequence read to occur in the neighboring region of the end of the contig that is represented by the external cloud. This use of external cloud the help to eliminate false branches into eliminate false reads and k-mers that might be added to the external cloud.

This example is shown for a branch, but is equally applicable to choosing a sub-branch. There can be instances where many first reads support only one branch, e.g., many support the next base being A. But, the number of first arm reads may be so high (e.g., exceeding a threshold, which may be related to an expected number determined from a number of cells) that all of the first reads cannot align to this part of the genome. Thus, some of the mate pairs actually correspond to different parts of the genome. It may be that the first reads are within a repeat region, and possibly the second reads extend past the repeat region.

In this case, there are multiple sub-branches, with the sub-branches corresponding to different sequences that are upcoming in the assembly process. The external cloud can be used to determine which sub-branch is most consistent with the external cloud. When the selection is only among sub-branches, the decision is not what base comes next for the contig, but what second reads to add to the external cloud. This has ramifications for future extension steps, which may require selecting between two different branches, which would affect the actual sequence. If the external cloud has invalid second reads added, this can cause a propagation of errors that leads to improper bases being used to extend the contig. Thus, such a process effectively determines which second reads to add to external cloud, when only selecting between sub-branches, and helps to preserve accuracy of second cloud.

The determination of which mate pairs correspond to which sub-branch can be made based on which second reads are consistent with the external cloud. If the second read matches to the external cloud, that mate pair can be considered part of the correct sub-branch. It can be acceptable to assign less than the expected number of reads to the correct sub-branch (e.g., only using 20 when the expected number is 40), if less than the expected number of second reads matched to the external cloud.

In one embodiment, if more than the expected number of second reads matched to the external cloud, the assembly process can stop, as this may be an indication that the cloud (and therefore the end of the contig) has been contaminated. The assembly process can stop at other times as well when data is not consistent, thereby preserving accuracy.

3. Retirement

The second reads of the external cloud can be removed from external cloud after a predetermined number of extension steps after they have been added. This is generally referred to as early-retirement herein. The early retirement allows for the external cloud to be smaller and less prone to being over-inclusive as to which branches or sub-branches to choose for adding new second reads to the external cloud.

With early-retirement, the second reads do not remain in the external cloud. Instead, any second reads of the general cloud can be compared to the end sequence; however, the second arm reads do not necessarily have corresponding first arm reads that align the internal cloud. In such a scenario, the corresponding first reads can be compared to the internal cloud as depicted in FIGS. 11A and 11B. Instead of early-retirement, the second reads can be kept in the external cloud until they are used to extend the contig, which is termed late retirement, as described in the section below.

4. Using Second Arm Reads of External Cloud for Extension

The second arm reads of the external cloud can remain in the external cloud until they reach the end sequence, and then used for extending the contig. This is referred to as a late retirement herein. As second arm reads are in the external cloud, it is known that the corresponding first arm reads are consistent with the contig because the first arm reads have already been aligned to the contig. Thus, the corresponding first arm reads can be explicitly added to an internal cloud or implicitly be known to be consistent to the internal cloud.

The alignment of a second read still in the external cloud would typically occur once a distance from the corresponding first read is the size of the mate gap. The second reads that align to the end sequence may overwhelmingly indicate a single branch. For example, more than 80% of the second arm reads may indicate that the next base is an A. In one embodiment, if the total number of reads of the other 20% is below a threshold (e.g., a threshold where the reads can be attributed to errors), then the strongest branch can be selected for extending the contig.

After the branches chosen based on aligning second reads of external cloud to the end the contig, first reads that are consistent with the selected branch can be identified. Then, the second reads corresponding to the first reads of the selected branch can be added to the external cloud, thereby replenishing the external cloud. Mate pairs can be removed from a general cloud when both reads of a mate pair have been used.

D. Helper Contig

In the examples above, the external cloud provided some information about upcoming genetic information that is beyond a current end of a contig being extended. Such information did not include a specific sequence that is expected, and possibly had gaps since the second reads were identified from mate pairs with first reads aligning to the contig. Other embodiments can provide a separate contig (helper contig) that has an order and less or no gaps (completeness), although the accuracy might be less than the active contig (i.e., the one being extended, and simply referred to as contig). The helper contig can be used to resolve branches for extending an active contig, e.g., as described herein. Helper contigs constructed with high accuracy (e.g., using same thresholds for assembling contigs) may be incorporated into the assembly with the active contigs.

Accordingly, in some embodiments, the external cloud can be assembled to create a helper contig, or a helper contig can be assembled in addition or instead of the external cloud. As one knows that the kmers of the external cloud are within the chromosome at some point forward, the kmers can advantageously be assembled before the contig actually reaches such a point. Such an assembly can be performed before or in parallel to the extension of the contig.

1. Building the Helper Contig

The helper contig (HC) can be temporarily made to guide the extension, but not to be used as a final contig. The helper contig can also be used in a more permanent fashion to directly extend the contig. The helper contig can be built in a similar manner as a seed is extended. The seed can be started from a second read of a mate pair, where the first read has been used in extending the contig. For example, a seed can be selected from the external cloud. In one implementation, a unique kmer is used as the seed.

The seed can be extended from both directions, similar to regular seed extension. Such extension may or may not use mate pairs, as the extension can just be from any read of a mate pair. Thus, for the helper contig, some embodiments may only use the read and label information. For example, labels to be used can be limited to those already included in the representative set for the growing contig, as these labels correspond to that region of the genome. The contig at this point can be a haploid contig, and thus there may be separate sets of labels for each haploid contig. The rest of the discussion will just consider one of the haploid contigs.

In one embodiment, the kmers in the external cloud can be used in assembling the helper contig. For example, an overlapping of the kmers in the external can be used to extend the helper contig.

The helper contig can provide order and completeness that might otherwise be missing in certain implementations of the external cloud. The completeness can be obtained by using any kmers having labels of the representative set, as opposed to just kmers from mate pairs used for the contig. As the helper contig is built with its own information, it can be complete as the operations that have been performed. Thus, the helper contig can be created from reads where no mate pair information is known.

The amount of effort into the helper contig can be less than the active contig, e.g., a little more error might be tolerated, since the helper contig might not be used to provide sequence, but just to help extend the active contig. Thus, in one implementation, when sequence of repeat is obtained, then the helper contig can be discarded. In other embodiments, the helper contig could be a separate active contig, with as much accuracy, and thus the helper contig could be used to provide the sequence in the next region. For example, the contig may hit the helper contig. Embodiments can track the reads so that two reads will not be used both to extend the contig and the helper contig.

Figure 13C:
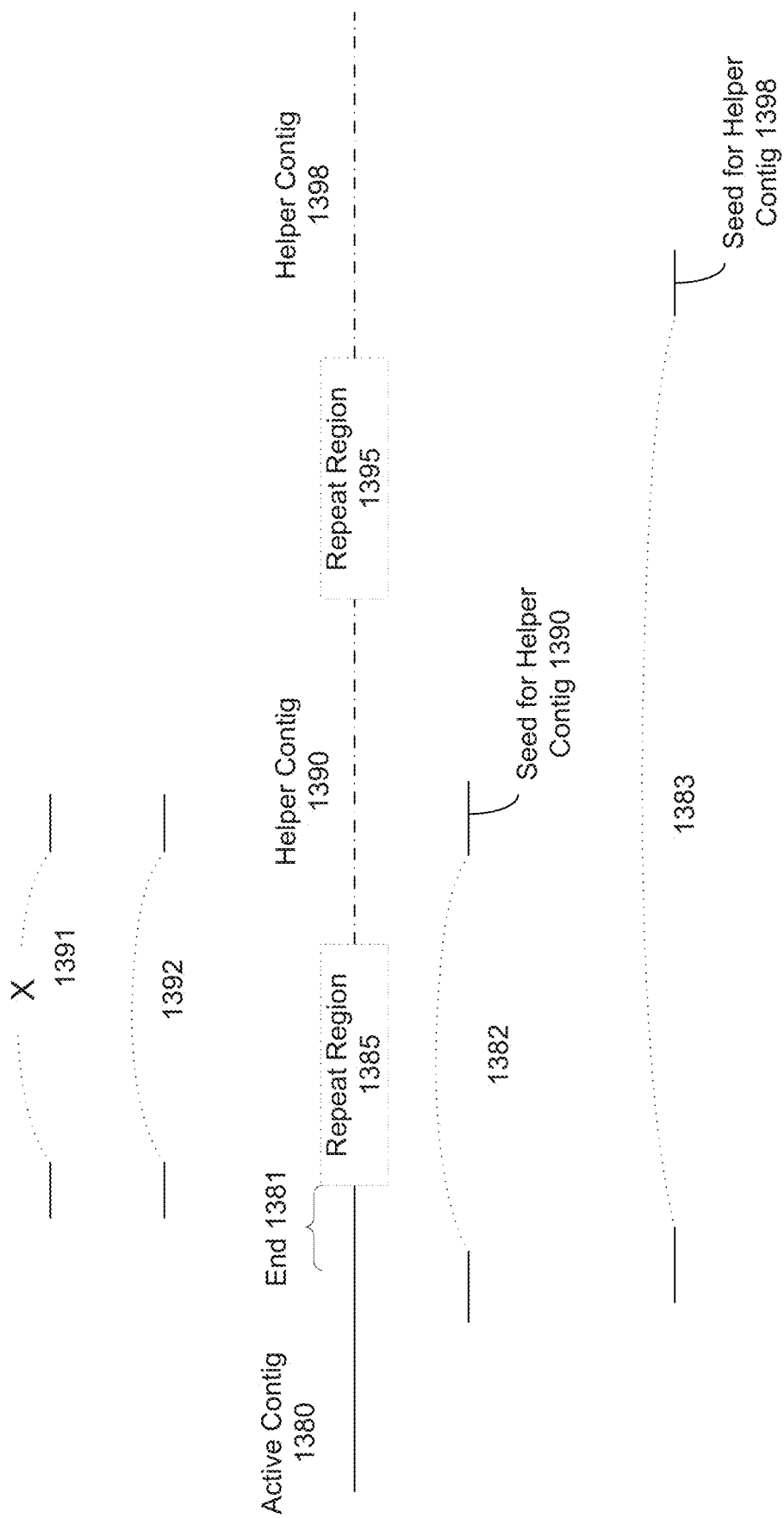
FIG. 13C shows creation and use of a helper contig according to embodiments of the present invention.

FIG. 13C shows creation and use of a helper contig according to embodiments of the present invention. An active contig 1380 has an end 1381 to which reads are being aligned for extending active contig 1380. A helper contig 1390 is separated from end 1381 of active contig 1380, although helper contig 1390 could extend to the left past end 1381, e.g., as active contig 1380 is extended. Helper contig 1390 is shown on the far side of a repeat region 1385 that is between active contig 1380 and helper contig 1390. However, the separation region does not have to be a repeat region. A repeat region has a similar sequence to many other regions in the genome. A helper contig can be used on both sides of active contig 1380.

A mate pair 1382 is identified with a first read that was used to create active contig 1380. The second read of mate pair 1382 can be used as a seed for creating helper contig 1390. The second read has not been used to extend the active contig, and given the expected length of the mate pairs, the second read is expected to be past the end 1381. Using the second read of mate pair 1382 can help to ensure that the helper contig is close to the end 1381.

In extending helper contig 1390, it can happen that repeat regions are hit on both sides, where extending past the repeat regions can be difficult. Further, there can be mate pairs that have a second read that do not align to helper contig 1390. For instance, the second read of mate pair 1383 does not align to helper contig 1390. In such a case, a second helper contig 1398 can be created. In another implementation, repeat region 1385 can be resolved using helper contig 1390, and then the active contig can be extended to repeat region 1395. At that point, helper contig 1398 can be created.

The helper contig can be of various lengths. In one embodiment, the helper contig may be extended for a distance comparable to the maximum mate pair distance (e.g., 1 Kb). Various techniques can be used to enforce this distance. In one embodiment, when the length of the helper contig reaches the maximum mate pair distance (or other distance), the extension of the helper contig can stop. The helper contig could extend past the end of the active contig. The helper contig could be retired after a certain number of extensions of the active contig, e.g., after the active contig has been extended 100 bases. Once an old helper contig is retired, a new helper contig can be created using a seed from a second read of a mate pair near the end of the active contig.

In another embodiment, when the length of the helper contig exceeds a threshold distance, older parts of the helper contig can be retired. A record can be kept of the position a read was added to the helper contig. The retiring can thus be of the parts of the helper contig that are closest to the active contig. In embodiments where the helper contig lies between two repeat regions, the helper contig can be as long as possible, and therefore extension beyond a threshold distance is desirable. In this manner, the helper contig can be used to distinguish fragments that fall in between two repeat regions.

The helper contig can be made in parallel or before extending the active contig. For example, a helper contig can be made on each side of a seed (i.e., a seed for the active contig). Once one or two helper contigs are available, the active contig can be grown.

In some embodiments, different zones can specify whether a helper contig is used. For example, in a green region, the contig growing will be done without the use of the helper contig. If entered into the yellow region, the helper contig is to be made and used. This is expected to make the extension possible. In the red zone, the extension of the active contig stops. Different conditions can define each region.

2. Storage of the Helper Contig

Once this helper contig is made, it can be stored in various ways. For example, the helper contig can be stored as a list of read IDs with arm designation and position in the contig. The list can be a sorted list that corresponds to the order of the genomic sequence in the region of the helper contig. The list can be function as an index. Thus, the helper contig can be stored differently than the active contig.

In one embodiment, the helper contig is implemented as a table with keys being the position within the contig and the values as follows: 1) kmer, 2) read ID, 3) position of the kmer within the read, 4) label. In lieu of alignment to contig (allowing mismatches), a search through this table can result in a fast alignment of a second read that is being used to determined which first reads should be used to extend the active contig. Such a table can also be used for the internal cloud, and for the contig, e.g., in lieu of doing an alignment against the contig.

3. Selecting Branch with the Helper Contig

The helper contig can be used to prove or disprove the new reads that are to be aligned to the end of the active contig. Suppose for a new mate pair, the first read matches the end of the active contig. Embodiments can then compare the other arm to see if it matches the helper contig, and a match is used as evidence that the first read should be accepted (e.g., the corresponding branch should be accepted). Thus, the second read of a mate pair could be used to select a branch when more evidence is from the reads of mate pairs used to create the active contig.

For example, assume that two branches exist for extending the active contig. Each branch has first reads that align to the end of the active contig. But, not all of the second reads may align to the helper contig. One branch can have all or a high percentage (or amount) of second reads aligning to the helper contig, while the other branch can have a lower amount of percentage of reads that align to the helper contig. The branch corresponding to the larger amount of second reads that align to the helper contig will likely be the correct branch.

FIG. 13C shows a mate pair 1392 of one branch, where mate pair 1392 has a second read that does align to helper contig 1390. Whereas, another branch has a mate pair 1391 that have a second read that does not align to helper contig 1390. Thus, the branch of mate pair 1392 can be selected as the correct branch for extending active contig 1380.

Since the helper contig provides a sequence, the matching can be more accurate than the identification that similar kmers exist in the external cloud. Further, as there is an order, a distance of where a second read matches to the helper contig can be used. For example, if the helper contig is longer than the maximum mate pair distance, an alignment of the second read to a far end of the helper contig can be weighted less since the mate pair would need to have a very large mate gap. An alignment that suggests a mate pair has a gap that is closer to an expected mate gap length can be weighted higher.

4. Repeats and the Helper Contig

As mentioned above, extension of an active contig can be difficult when a repeat region is encountered. The helper contig can be particularly helpful in such situations. As the second reads can uniquely be aligned to the helper contig, the first reads that correspond to the repeat region can be identified. This group of first reads can then be assembled to determine the sequence of the repeat region. Since the group of first reads correspond to second reads that align to the helper contig, the group of first reads is trustworthy. In one embodiment, if the repeat region is too difficult to assemble, the helper contig can be used as a new seed for a new contig, and the repeat region can be skipped.

Some examples of repeats are as follows. One example is two neighboring (e.g. at 1 to 100 base distance) repeats longer than a read length but shorter than the mate pair length; e.g., two repeats each with 300 bases in length separated by 100 bases. Another example is two repeats longer than mate pair length, where the two repeats occur within about 5 kb-50 kb, e.g., two repeats each with 5 Kb length, separated by 50 Kb. Another example is a maximum likelihood estimation of reads recruited to two neighboring repeats. A repeat region can be identified when the number of matching kmers and/or reads (e.g., one kmer with many reads) is very large (e.g., 2 or 3 times the sequencing coverage, or even 1,000 times the sequencing coverage).

FIG. 13C shows two repeat regions 1385 and 1395 and two helper contigs 1390 and 1398. One does not know a priori which helper contig is actually closer to active contig 1380. The closer helper contig should have more second reads that align to the closer helper contig, i.e., second reads corresponding to first reads that align to active contig 1380. Thus, helper contig 1390 should have more second reads that align to it, than align to helper contig 1398.

In one example, there are two repeats that are shorter than a mate pair, longer than the read, and they are in a short distance to each other, e.g., shorter than the mate pair. For instance, each repeat region is 300 bases and the distance apart is 200 bases (e.g., helper contig 1390 is 200 bases). Assume that repeat region 1385 and 1395 are identical except that repeat region 1385 has an A at a location where repeat region 1395 has a G.

Embodiments can identify that repeat region 1385 is more connected to helper contig 1390 as more second reads of mate pairs with first reads with the A align to helper contig 1390 than align to helper contig 1398. And, G has more second reads that align to helper contig 1398. Thus, the order information of the helper contig can help to identify which helper contig is closer to the active contig, and differentiate between repeat regions that differ by just a few bases.

In another example, assume that there are tandem repeats that are within the expected mate gap distribution. To resolve this problem, a helper contig can be made for the unique area in between the repeats. Then, one identifies if there is label (e.g., a well) whose long fragment ends in between the repeats. This can be done by assembling the reads of each label separately, and the end of the assembled sequence for a particular label would correspond to a middle part of the helper contig. The reads of from this label can then be used to identify a unique feature in the first repeat region since its reads do not include the second repeat region, thereby determining an order to the repeat regions.

E. Method Using Mate Pair Information

Figure 14:
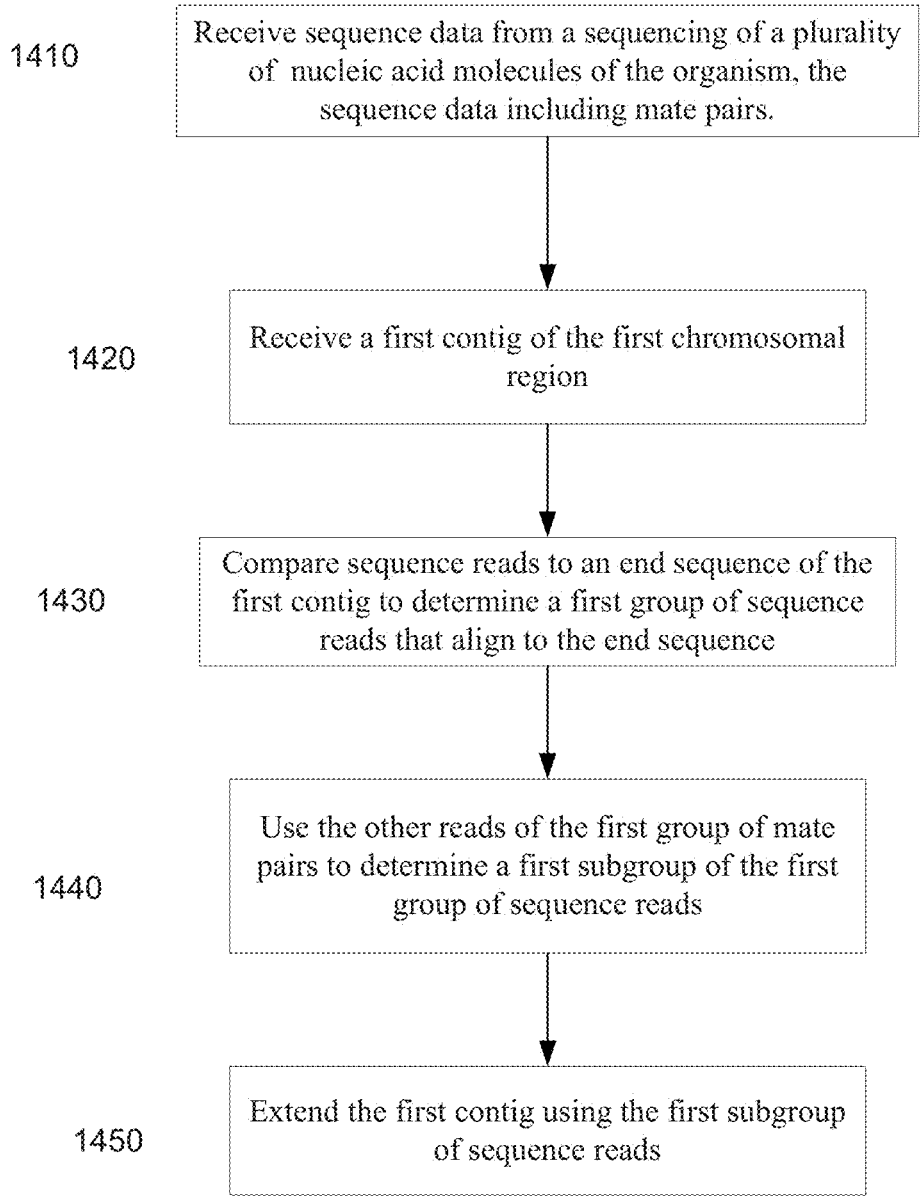
FIG. 14 is a flowchart of a method 1400 of assembling a sequence of a first chromosomal region of an organism using mate pair information according to embodiments of the present invention.

FIG. 14 is a flowchart of a method 1400 of assembling a sequence of a first chromosomal region of an organism using mate pair information according to embodiments of the present invention.

At block 1410, sequence data is received from a sequencing of a plurality of nucleic acid molecules of the organism. The sequence data for each of the plurality of nucleic acid molecule includes a mate pair of sequence reads. The mate pair includes a first read of a first part of the nucleic acid molecule and a second read of a second part of the nucleic acid molecule. The second part is after the first part in the first chromosomal region.

At block 1420, a first contig of the first chromosomal region is received. The first contig can be received correspond to a seed or any contig at various parts of the assembly process.

At block 1430, sequence reads are compared to an end sequence of the first contig to determine a first group of sequence reads that align to the end sequence. The sequence reads of the first group all from a corresponding part of the nucleic acid molecules. That is, all the sequence reads of the first group are first reads or all of the sequence reads of the first group are second reads. The first group of sequence reads is from a first group of mate pairs;

At block 1440, the other reads of the first group of mate pairs are used to determine a first subgroup of the first group of sequence reads. For example, the other reads can be second reads, when the sequence reads in block 1430 are first reads. The second reads can be compared to the external cloud to determine which first subgroup (e.g., which branch or sub-branch) to use to extend the contig, e.g., as depicted in FIGS. 11A and 11B. As another example, the other reads can be first reads, the sequence reads in block 1430 are second reads. The first reads can be compared to the internal cloud to determine which branch or sub-branch to use in extending the contig, e.g., as depicted in FIGS. 13A and 13B At block 1450, the first contig is extended using the first subgroup of sequence reads. In some embodiments, both first reads and second reads are aligned to the end of the contig. Support for each branch can be measured by the number of first reads that align to the internal cloud and the number of second reads that align to the external cloud. In one implementation, equal weighting is provided to first reads that align to the internal cloud into second reads that align to the external cloud.

In another implementation, more weight can be given to first reads that align to the internal cloud, as entire sequence read can be aligned, whereas it is unlikely that an entire second read were aligned to another second read in the external cloud. Instead, a k-mer of the second read would likely be matched with a k-mer in an external index. This greater weighting of alignment of first reads to the internal cloud can be effectuated by using only alignment of the second reads to the end of the contig to determine which branch to select. Then, second reads can be added to the external cloud by determining first reads that correspond to the selected branch, where the second reads of the selected mate pairs are consistent with the external cloud.

F. Retirement with Indexes

The retirement of the sequence read from a general cloud, an internal cloud, or an external cloud can be performed separately or in conjunction with the retirement of a k-mer from the general index, an internal index, or external index. In one embodiment, when a k-mer is selected for a branch to extend the contig, a general index that includes the k-mer can be updated to remove any reads of the selected branch that include the k-mer. For example, the k-mer may correspond to 100 first reads, but only 20 of the first reads may correspond to the selected branch (e.g., when only 20 the second reads matched to the external cloud). In this case, the general index may be updated remove those 20 reads from the k-mer (e.g., stop associating those 20 reads with the k-mer).

For retirement from the internal index, a k-mer can have an associated counter that corresponds to a number of extension steps. When a k-mer is used to extend the contig, the counter may be set to zero. Then, for each extension step that does not include the k-mer, the counter can be increased. In one implementation, the k-mer can be immediately added to the internal cloud, or added to the internal cloud when the counter reaches a particular value, which corresponds to the internal cloud starting a specified distance away from ends 1005 and 1025 of the contig (as depicted in FIG. 10A). When the counter exceeds a threshold, the k-mer can be removed from the internal cloud. If the k-mer is used again to extend the contig while the k-mer is still in the internal cloud, the counter can be reset to zero.

A similar technique can be used for the retirement from the external index as is used for the retirement from the internal index. For example, when a k-mer is added to the external index, a counter may be set to zero. When the counter exceeds a threshold (which may be proportional to the mate pair gap or length), the k-mer can be removed from the external index. If a k-mer of the new sequence read matches to the existing k-mer of external index, the counter for that k-mer can be reset.

In this manner, the same k-mers are not be discovered again and again, which can cause errors. Retiring k-mers as opposed to an entire sequence read can be advantageous. An advantage of a k-mer is that a part of your read can be broken (e.g., due to bad synthesis or bad sequencing), and yet other parts of a read may be good. Further, other k-mers of a read may still be used after one k-mer of the read is retired.

Further, labels can be retired from the representative set based on k-mers. When no more k-mers with a particular label are in the internal cloud, then the label can be removed from the representative set. The label could be removed also when number of k-mers is below a threshold number.

G. Scores

A score for the comparison of arm reads to an internal/external cloud can be determined in various ways. For comparison to the internal cloud, all of the bases of the sequence read can align to a sequence of the internal cloud. Such alignment can provide a higher score for consistency with the internal cloud. Any mismatches can reduce the score. Further, if an internal k-mer index is used, a score can be based on the number of k-mers of a read that matched to a k-mer in the internal index. The score for the comparison to the external index can also be based on the number of k-mers read that matched to a k-mer in the external index.

The scores can be used to determine which branch or sub-branch to take. The mate pairs with the highest scores can be used. For example, the scores for all the reads of branch 1 can be added to provide a first sum, and the scores for all the reads of branch 2 can be added to provide a second sum. The first sum and second sum can be compared, and the branch corresponding to a larger value can be selected.

A minimum value can be required for selecting a branch. If the minimum value is not satisfied for any branch, the extension can be stopped.

VIII. K-Mer Indexes

The use of k-mer indexes has been described above. As examples, a k-mer index can be used to identify reads that align to the end sequence of a contig, determine whether a read of a mate pair aligns to the contig (e.g., using an internal index), and determine whether a read of a mate pair is consistent with upcoming parts of the contig (e.g., using an external index).

K-mers can be useful in that one error in a read can cause problems for alignment. If the reads are relatively long, there can be an unacceptable probability that at least one error exists. The smaller k-mers will have a less likelihood that an error exists, as they are smaller. Thus, a k-mer index can provide more redundancy, and can allow one to catch more errors.

Additionally, a k-mer index can identify alignments to multiple reads in one operation. For example, when the alignment is made to a particular k-mer, an alignment can be made automatically to all the reads associated with that k-mer. Besides being associated with multiple reads, a k-mer can be associated with one or more labels (e.g., each label being associated with particular read that includes the k-mer). A k-mer index can also include a position of the k-mer for particular read, and can include a memory address of the read.

A. Types of Indexes

There are various indexes that may be used. Indexes can vary based on the type of information that is stored in an index. An index can also vary based on which reads are used to create the index. For example, an internal and external index corresponds to different parts of the contig.

1. Read/General Index

A read k-mer index (RKI or ReadIndex) corresponds to an index of k-mers (e.g., 17-mer) for the reads. FIG. 4A provides one example of a structure of the RKI. In one aspect, the RKI can include k-mers from any read that may be aligned to the end of a contig. For each read, contiguous parts (e.g., 17 contiguous bases) may be used to determine the various k-mers in the read. In each contiguous part, a sliding window of k-mers can be found. For example, if a read has 25 bases and the k-mer index is 20, a first k-mer is the sequence from position 1 to position 20; a second k-mer is from position 2 to position 21; and so on. Non-contiguous parts of the read can also be used to determine k-mers.

Each k-mer, along with its position on the read, a read ID or address, and a read label can be saved in an index. If all the reads are the same length, the retrieval of a read from memory can be hard-coded to retrieve the same amount of data, but with the address being specified to identify which data to retrieve. If reads are difference lengths, data specifying a length of a read can be stored in an index, or at the memory address, thereby indicating how much data to retrieve.

Some embodiments can remove k-mers that have more than a threshold number (e.g., 50 or 100) of associated reads. Such k-mers may correspond to repeat regions of the genome. Thus, the k-mer can be repeated too many times to provide an accurate assembly. The assembly process can identify such a situation where the k-mer information would not provide accurate assembly in a region. The deletion of such k-mers allows the index to become smaller and faster. In one implementation, such k-mers can be saved in a separate index, and used to fill in parts of a genome between contigs, e.g., at a point in the process where assembly has already occurred, thereby allowing more control of errors that such repeat regions might cause.

2. Reference/Genome Index

The genome k-mer index (GKI or GenomeIndex) corresponds to an index for a reference genome, which can be used in certain circumstances, as is described herein. For the genome, a sliding window of k-mers can be defined. For each k-mer, the position on the genome is saved in the index. Each k-mer can be associate with multiple positions at which the k-mer can be found (e.g., each position being effectively stored as a different column). Implementation of GKI is similar to that of the RKI, except instead of reads a sliding window (1-base at a time) on the genome is used.

In one embodiment, a genome k-mer count index (GKCI, GKC or GenomeCount) can store the number of reads for each k-mer. The number of reads can be stored in a separate index or in a column of the same k-mer index. This information can provide greater efficiency so that the number of hits for each k-mer can be obtained from here without pulling all the reads that match to the k-mer. The number of reads can be useful for various purposes. For example, the reads for a k-mer can be stored contiguously such that all the reads can be obtained in one read request, where the number of associated reads can be used to specify how much data is requested. As another example, the number of reads that include the k-mer can be used to identify repeat sequences in the genome when the number is high (e.g., above a threshold).

3. Internal and External Clouds

Internal and external clouds and discussed above, and may be implemented as internal and external indexes. These indexes can be of a different size than the RKI. For example, the RKI can use k-mers of length 17 bases, and the internal and external indexes can use k-mers having a length of 12 bases. The external and internal indexes can also use different length k-mers.

As a contig can be extended to the left and to the right, there can be a left and right index for both the internal and external indexes. For example, there can be a left internal index and a right internal index, as well as a left external index and a right external index.

In one embodiment, a left external index (LEI) would correspond to an index of k-mers for the left arm of the reads (also referred to more generally as first reads herein). LEI is made when the extension is toward left. The reads that have the right arm (second read) on the contig will contribute their left arms to building LEI. The left arm can be scanned for k-mers and placed into the index. If the length of the contig is short, the cloud may be allowed to only grow. However, if the length of the contig is very long (e.g., significantly beyond the length of mate pair), then the cloud can be trimmed by retiring the reads/k-mers that were added first, e.g., corresponding to the parts that are closest to the contig. Such retirement is also described elsewhere.

A right external Index (REI) would correspond to an index of k-mers for the right arm of the reads. REI can be made when the extension is toward right. The reads that have the left arm on the contig, will contribute their right arms to building REI. The right arm can be scanned for k-mers and placed into the index. Retirement can occur in a same way as for the LEI.

B. Read Address

FIG. 15A shows an example k-mer index 1500 with read addresses stored for each k-mer according to embodiments of the present invention. The first column 1501 shows a list of k-mers, where the list can be sorted by certain criteria for faster searching. Each of the other columns corresponds to a different read that includes the k-mer of that row. As shown, the value stored for each read is a memory address from which the read can be retrieved. The memory addresses can be in any suitable form, e.g., hexadecimal, decimal, etc.

As with FIG. 4A, the number reads for each k-mer will vary, where empty slots are indicated with "-". These anti-slots would not actually store any data, and the overall size of the index can be compressed. In effect, each row can be stored after each other where the next row begins after the previous row ends. Such storage can use a number of total reads for a particular k-mer entry to differentiate reads of one k-mer from another.

In one embodiment, the reads can be stored in memory, each having a memory address. Each sequence read can be analyzed to identify one or more k-mers within the sequence read. The k-mer index can be generated by: for each k-mer, storing, in the k-mer index, one or more memory addresses of sequence reads that are identified as including the k-mer. For example, a particular k-mer might be found in 4 reads, and the memory address for each of the 4 reads is stored in association with the k-mer (e.g., stored as part of a k-mer entry in the index). The k-mer index can be stored in the same memory (e.g., RAM, ROM, flash memory, or the like) as the reads.

The number of reads would typically be quite large, e.g., providing more than 10×, 20×, 30×, or 100× genome coverage. Additionally, the k-mer index can include a substantial portion of all k-mers that exist in the reads (note that more k-mers can exist than are identified). For example, more than 10%, 25%, or 75% of all k-mers that exist in the reads can be found in the index. The number of k-mers that exist is dependent on the size of the reads and the length of k-mer being used, and can depend if the k-mers are restricted to contiguous bases. For example, if the k-mers are restricted to contiguous bases, the total number of k-mers that exist of 1,000 reads of 25 bases, where the k-mer is 20 bases, is at most 6,000. But, a k-mer may appear in more than one read, and thus the total number might be less.

Having the memory address be the read identifier allows for a faster retrieval from memory. For example, the memory address can be obtained from the index of that included in a request sent to a memory controller, which can use the memory address to resolve which data is being requested. No intermediate resolution of an identifier to a memory address would be needed, therefore providing more efficient retrieval.

C. Position of k-Mer in Read

Instead or in addition to a memory address, a k-mer entry can include a position in the particular read that a k-mer can be found. The position can be used for various purposes, such as identifying whether the read is a first read or a second read (e.g., left arm read or right arm read) of a mate pair. This data can allow for searches of only first reads or second reads, which can be advantageous in implementing methods described above for mate pairs.

FIG. 15B shows an example k-mer index 1559 with read addresses stored for each k-mer according to embodiments of the present invention. The k-mer index 1550 has a similar organization to FIG. 15A, with an extra column 1552 of read position. Thus, for every k-mer, it is known where the k-mer can be found in each of the associated reads. In one implementation, the position can correspond to where the first base of the k-mer occurs in the read.

In some embodiments, a mate pair can be stored next to each other in memory, and the position can indicate which read of the mate pair the k-mer can be found. For example, second associated read of k-mer 1 has a position 26, which can indicate that corresponds to a second read when each read of a mate pair is 25 bases.

In one embodiment, clones can be removed in the following manner. If for a specific k-mer the position within the read is the same, the two reads can be flagged as possibly being clones. In one implementation, the two reads can immediately be identified as clones, but another limitations further analysis of the entire read can be performed to identify whether they are clones. If two or more reads are identified as being clones, an embodiment can store just one read. For example, one read is selected as a representative read and the rest are discarded. Alternatively, the representative read is made by combining multiple reads (e.g., averaging).

D. Labels in Index

As mentioned above, the label corresponding to a particular read can also be stored within an index. In this manner, k-mers that have a particular label (e.g., a particular well) can be identified using the labels. Such a search can be used in finding k-mers that have labels corresponding to the representative set of labels of the contig.

FIG. 16 shows an example k-mer index 1600 with read labels stored for each k-mer according to embodiments of the present invention. As shown, each read is followed by a label and a read position, although various combination can be used, e.g., just a read identifier and a label. The label can use any suitable symbol, such as numbers, letters, hexadecimal, etc.

As above, each sequence read can be analyzed to determine a plurality of k-mers. Each k-mer would typically be smaller than a length of the sequence read from which the k-mer was determined, but may also be equal in length to the read. The label of the sequence read is associated with the plurality of k-mers as part of an index. For example, the read would be added to the k-mer entry in the index for each k-mer within the read. Thus, the label for a read would be associated with each k-mer of the read.

E. Extending Using k-Mer

Regardless of which type of information is stored in the index and the type of the index (e.g., internal/external index or read index), a k-mer index can be used to identify sequences for extending the contig. The extension can be performed in various ways.

In one embodiment, once the matching k-mer is identified, the corresponding reads can be retrieved and compared to the end of the contig. In this manner, the extension can depend on the position of the k-mer in the read, as there may be multiple bases (neighboring bases) after the k-mer on the aligned read. In another implementation, the extension can still be the same amount for each step.

In another embodiment, the k-mers can be larger than the end sequence. For example, 20-mers can be aligned to the last 19 bases of the contig, with any of the matching 20-mers being used to extend the contig (e.g., selecting a specific 20-mer to extend the contig). The number of bases for extension can depend on the number of bases in the end sequence, which can be any number of bases less than the k-mer (e.g., 2, 3, or 4 bases less). When extending by more than one base, the number of branches can be more than 4, and may be $4^N$, where N is a number of bases for the extension. In this embodiment, the k-mer that corresponds to more sequence reads having one of an expected set of labels (which may be the specified labels) can be used to extend the contig.

When the index includes labels, the extension can include accessing the index in the memory to determine a first set of sequence reads having a k-mer that overlaps with an end sequence of the first contig. The number of sequence reads having one or more specified labels (e.g., the representative set of the contig) can be used to select a branch, as is described herein. As another example, the first set may correspond to only one specified label when contig is being determined for a single aliquot. In one implementation, the k-mer index can be searched only for reads having one or more specified labels, thereby improving the efficiency of the search.

In one embodiment, the first set of sequence reads can have a same k-mer that matches to k bases of the end sequence, where the neighboring bases of the reads are used to extend the contig. In another embodiment, the first set of sequence reads correspond to at least two different k-mers that overlap with k−1 bases of the end sequence (or a smaller number of bases of the end sequence, such as k−2).

The first set of sequence reads can be a subset of a larger set (superset) of k-mers that overlap with the end sequence of the contig. The first set can be identified from the superset as the sequence reads that have the one or more specified labels.

The index may also include information about the quality of the base calls for a particular k-mer for a particular read. In one embodiment, reads with higher base call scores can be given higher weight when determining which branch to take. In some implementations, a read may be added to a k-mer index only when the base call scores are above a threshold. As another example, reads with a high enough base call score can be identified in the index (e.g., the quality score is included in the index) and only those reads used to select a branch.

F. Multiple Indexes

In some embodiments, indexes of different sizes can be used. For example, one can use a 17-mer index and a 20-mer index. In one embodiment, probabilistic hash tables can be used to reduce the storage size of the indexes. Using such techniques, a penalty might arise the k-mer might occasionally be missed, but such a mess may only happen at a relatively low percentage (e.g., 1%).

G. Local Kmer Index

As mentioned herein, repeat regions can be difficult to assemble. For example, an ALU repeat can be about 300 bases and appear about one million times in a human genome. But, each repeat may differ slightly by length and/or a few bases. Such repeats can be 10 kb apart.

When a contig hits such a repeat, a kmer than aligns to the end of the contig can be associated with many reads (e.g., thousands or millions of reads). As another example, a second read (e.g., right arm read) can align to the end of the contig, but the corresponding first read does not align to the contig. To use that kmer in extension, all of the reads will need to be sorted through, which is computationally expensive. And, many of the reads will not be the correct one that actually corresponds to the specific repeat region that occurs at the end of the current contig.

To address this problem, embodiments can identify reads that are local to the end of the contig, and then only use those reads. These reads can be used to form a local kmer index that is specific to the repeat at the end of the contig. Since the number of reads associated with the kmers in the local kmer index is far less than the general kmer index, searching through the index is much faster. Other embodiments can use the local reads without implementing an index.

In one embodiment, the local reads can be identified using the active contig and a helper contig, which is discussed above. For example, referring back to FIG. 13C, assume that helper contig 1390 has been created, and we are trying to assemble repeat region 1385. One can align second reads to helper contig 1390. The second reads that are used in creating helper contig 1390 can be identified. Or, one can align new reads to helper contig 1390.

The corresponding first reads of the identified second reads are thus known to occur to the left of the identified second reads. The corresponding first reads can be identified using mate pair information. At least some of these first reads will be from repeat region 1385. Some may align to active contig 1380 and some to helper contig 1390 itself, but some will align to repeat region 1385.

The number of identified first reads and second reads local to repeat region 1390 is a manageable number. Thus, the local first reads can efficiently be assembled to determine the sequence in repeat region 1385. For example, the first reads can be aligned to the end 1381, to an end of helper contig 1390, and to each other.

And, the second reads corresponding to first reads that are aligned to the end of the contig can be used for assembly of repeat region 1385. These second reads are also local to repeat region 1385, given that the first reads align to the end of the contig. These second reads of a first group with first reads aligning to the end of the contig and the first reads of a second group with second reads aligning to the helper contig can be used in the local kmer index.

In an implementation using a local kmer index, the number of reads for any given kmer is relatively small. Thus, when a kmer in the local kmer index is found to align to a particular sequence (e.g., end 1381), the kmer will be associated with a relatively small number of reads (e.g., thousands compared to millions). Thus, the reads can be identified quickly, and there is a higher probability that the identified reads actually align to the extension position. The kmers in the local kmer index can be of different length than in the general kmer index. In one embodiment, the local kmer index can be built once the number of reads associated with an aligned kmer is above a threshold number (e.g., tens of thousands or a million).

IX. Combined Techniques

All of the various techniques described herein can be combined in various ways. For example, indexes may be used to efficiently identify alignment among sequence reads. Labels can be used to identify reads that are likely from a same long fragment, and thus correspond to reads already used in creating the contig. The use of such labels can differentiate among branches, and in particular, the labels can be used to the contig is relatively short.

Further, mate pairs can be used to select among branches or among sub-branches. In particular, mate pairs may be useful when repeat regions are encountered. For example, about 30% of the genome may be repeats, with some of the repeat regions capable of being assembled using the internal and/or external indexes. For instance, short tandem repeats may be addressable by mate pairs, and long repeats may have differences that allow assembly.

A. Combination Method

Techniques described herein can be combined in various ways. One embodiment for de novo assembly can proceed as follows. Various parts of implementations and details described below can be used in more general methods described above.

At step 1, a k-mer (e.g., 17) is defined for indexing all the reads. The k-mer size can also be used for indexing the genome reference.

At step 2, a k-mer index is made from the reads of the sample. A separate k-mer index can be made from the reference genome. A k-mer index can be made from both reads of the sample and the reference genome. The k-mer index can have properties described herein.

At step 3, a set of k-mer seeds is made of the genome for the sample organism whose genome is being determined from a sample. This set can be refined using the labels and any other read information for that specific k-mer. The resultant set of k-mer seeds can have expected conditions, e.g., number of labels and/or reads.

At step 4, each k-mer seed is expanded from both sides, one side at a time, and can alternate between sides. The seed growth can be supported by the k-mer alignment to the ends, the labels of the corresponding reads, and also by mate pair information, as is described for various embodiments. The contigs that are grown may be stopped by various violating conditions.

At step 5, when a polymorphism is hit, the contig may be "unzipped" from that point on, using the haplotype information. Further "unzipping" can be prevented (on a contig) as it is not biologically viable (only 2 haplotypes are allowed) when the organism is diploid. Unzipping can also occur at a later stage using the identification of any polymorphisms.

At step 6, the resultant contigs are stitched together using label and mate-pair information. The stitching can be done two at a time, which may be done with no scaffolding. This stitching can result in longer contigs (super-contigs).

At step 7, super-contigs are mapped to the reference genome and variations are declared. The mapping to the reference genome can use the k-mer indexes. The identification of the variations can help identify mutations and possible disease states.

B. Main Contig Growing

A contig can be extended according to the following embodiments. The main contig growing (MCG or Contig-Growing) algorithm can start with a seed and grow the seed as much as possible. A seed can be grown from left or right. Different regimes can be devised for doing so. One way is to take a step in the right direction followed by taking a step in the left direction. Seed extension can occur as described below.

On each side, MCG can stop if one of the following occurs: (1) It hits a repeat region, which may be marked by a large number of recruited k-mers from RKI, (2) It renders no results (lack of reads), e.g., no branches that satisfy alignment or other criteria, (3) The candidates are ambiguous, e.g., >2 haplotype candidates, (4) Candidate wells are inconsistent with an expected number of labels.

In various embodiments, MCG can use different information depending on the current contig size. If the contig size is short, a short contig growth (SCG) algorithm can be used. If the contig size is long (e.g., more than 1,000 bases), then a long contig growth (LCG) algorithm can be used. MCG can continue in a diploid (zipped) fashion until it hits a polymorphism. When a polymorphism occurs, it provides an opportunity to unzip the contig, i.e., convert it to two haploid contigs. Therefore, the algorithm proceeds to the unzipping step.

1. Seed Extension

In the seed extension step (SES or SeedExtension), seeds are extended from both directions. Each extension can be done for M, M−1, . . . , 1 bases, e.g., where M is 4. For each extension, one could either start with M and go down to 1, or do the opposite. The former can be most accurate but slower, and the latter can be less accurate but faster.

To start, embodiments can consider the former case, i.e., start with M bases after the k-mer. If there were not enough k-mers with M extensions available, M−1 can be considered. This process can be repeated until M=1. If M=1 does not have enough reads to support, the process can stop.

Alternatively, all 1 . . . M scenarios (i.e., different number of bases for extension are different scenarios) can be exhaustively explored, and compared for consistency, in order to achieve extra validation. At each M, $4^M$ conditions can be tested, corresponding to number of possible branches. There may be only 1 or 2 conditions satisfied for each of the $4^M$ conditions. For each combination of $4^M$ branches, the informational support of the extension is evaluated. The support of the extension can use labels and the representative set of labels. The k-mers or reads that were used in a successful growing step may be retired according to techniques described herein.

2. Short Contig Growing

In a short contig growing (SCG or ShortGrow) algorithm, the current contig is short, and therefore mate pair information may not be fully utilized. The extension is based on the labels of the aligned reads and the representative set of labels of the contig.

3. Long Contig Growing

In the long contig growing (LCG or LongGrow) algorithm, the current contig is long, and therefore mate pair information can be fully utilized, in addition to the information that is available for SCG algorithm. In one implementation, assuming the contig is long and the current extension is on the right side, the following can be done:
(a) Candidate reads with k-mers from RKI can be identified, and filtered using EW (i.e., representative set).
(b) From the reads in Step a, the reads that have the matching k-mer on their right arm can be identified.
(c) For the reads in Step b, the corresponding left arm can be identified.
(d) Overlap of the left arms in Step s can be validated via the appropriate cloud (e.g., internal cloud when extending to the right). If the extension is being done on the left side, the above steps can be switched.

Additional or different steps may be performed as described above for mate pairs. All of the reads, index, and labels can be stored in RAM, thereby allowing efficient access and accuracy by allowing all criteria to be used for each step. For example, the RAM can be accessed by a same set of one or more processors, e.g., as a symmetric multi-processing (SMP) node.

4. Universal

Universal contig growing (UCG or UniversalGrow) is a hybrid of short and long contig growing. The overlap finding is done implicitly, using clouds. Each side of the extension (Right and Left) will have an internal and external cloud for a total of 4 clouds. As the extension is done on each side, the internal and external clouds on that side are updated. This can be done from the first iteration. The clouds may not be useful until they contain a critical mass. The overlap of the other arm to the existing contig can be done using the internal or external cloud, in an implicit and fast way, e.g., using indexes.

5. Retirement

It may be possible that can keep all of the reads in an index without problems, but for very long contigs this would likely cause a problem. Thus, read retirement (RR or Read-Retirement) may be performed. If applied to the seed growing step, (subject to further analysis,) one of the following regimes may be applied after a successful growing/extension step: The whole arm of a read is retired from RKI, or only the corresponding k-mer in the read is retired from RKI.nnIf applied to the contig stitching step, when the read is used to successfully stitch two contigs, the whole read can be retired.

Retirement can be based on length or number of extension steps (each k-mer can have a counter). For example, there can be one counter that is tracked for each read. There can be one counter per read or could have a group number for all k-mers added at a same step, and thus one counter for all those with the same group ID. For example, when a counter gets above 1,000, then the read can be removed. Retirement can be from any index. Even RKI can have k-mers (or at least read associated with k-mer) removed.

C. Contig Stitching

In a contig stitching step (CSS or ContigStitching), contigs can be stitched together using the effective wells (labels) on the ends of contigs. Since the contigs' ends are within the average fragment length, it can be assumed that the corresponding ends should come from the same fragments, and thus a representative set of labels may be used, as described above. The stitching can provide super contigs, which can still be considered contigs.

Contig stitching could be done for two contigs at a time, or a collection of contigs. Different stitching methods can be performed for when the ends of contigs have different forms, e.g., one is unzipped to haploids and the other is not.

In one embodiment, if two contigs are next to each other, an embodiment can stitch them by having a first read of a mate pair on one contig and the second read on the other contig. It can be difficult to know which contigs are next to each other. In one embodiment, the contigs can be aligned to a reference genome to determine contigs that belong in the same region of the genome.

As an example, the end of one contig can be used to determine k-mers that align. The reads corresponding to the matching k-mer can then be found, and the mate pairs can be identified. The other reads (and corresponding k-mers) of the mate pairs can be used to determine if they align to the end of the other contig or any sequence within the contig. This alignment can be performed by comparing the other read to the internal index of the other contig. As another example, the alignment can be performed by comparing the external cloud of one contig to the internal cloud of the other contig.

In one embodiment, the stitching can connect two contigs, but a gap may still exist between the two stitched contigs after the initial connection. A this point, such a gap can potentially be filled in using knowledge of the labels and mate pairs corresponds to reads used to build the ends of the two contigs.

D. Length and Accuracy

The length of the contigs (including super contigs) can vary between samples and between different parts of the genome for a given organism. Contigs greater than 100 Kb or 1 Mb can be achieved. In one embodiment, the N50 value is longer than 100 Kb or 1 Mb. An accuracy of less than 1,000 or 300 errors per individual human genome can be obtained.

E. Use of Reference

In one aspect, de novo assembly can reduce bias that might otherwise be caused by the reference, if a read were initially aligned to the reference. But, the reference can be used at later stages, e.g., to help stitch together contigs, as is described above. The reference can also be used to select a seed. Some additional uses are mentioned below.

1. Growth

In one embodiment, if there are two different branches that are equally supported, then the branch that corresponds to the reference can be selected for extending the contig. Since the reference is not used to determine the branch, but just used to select which one is most likely, any bias from the reference is reduced.

2. Variation

Variations are defined with respect to a reference. With relatively long de novo contigs, they can be mapped back to the reference to identify a variation. Long contigs make it easier to map back to reference. Within those contigs, one can detect insertions and deletions relative to the reference by aligning a long sequence to the reference.

X. Computer System

Figure 18:
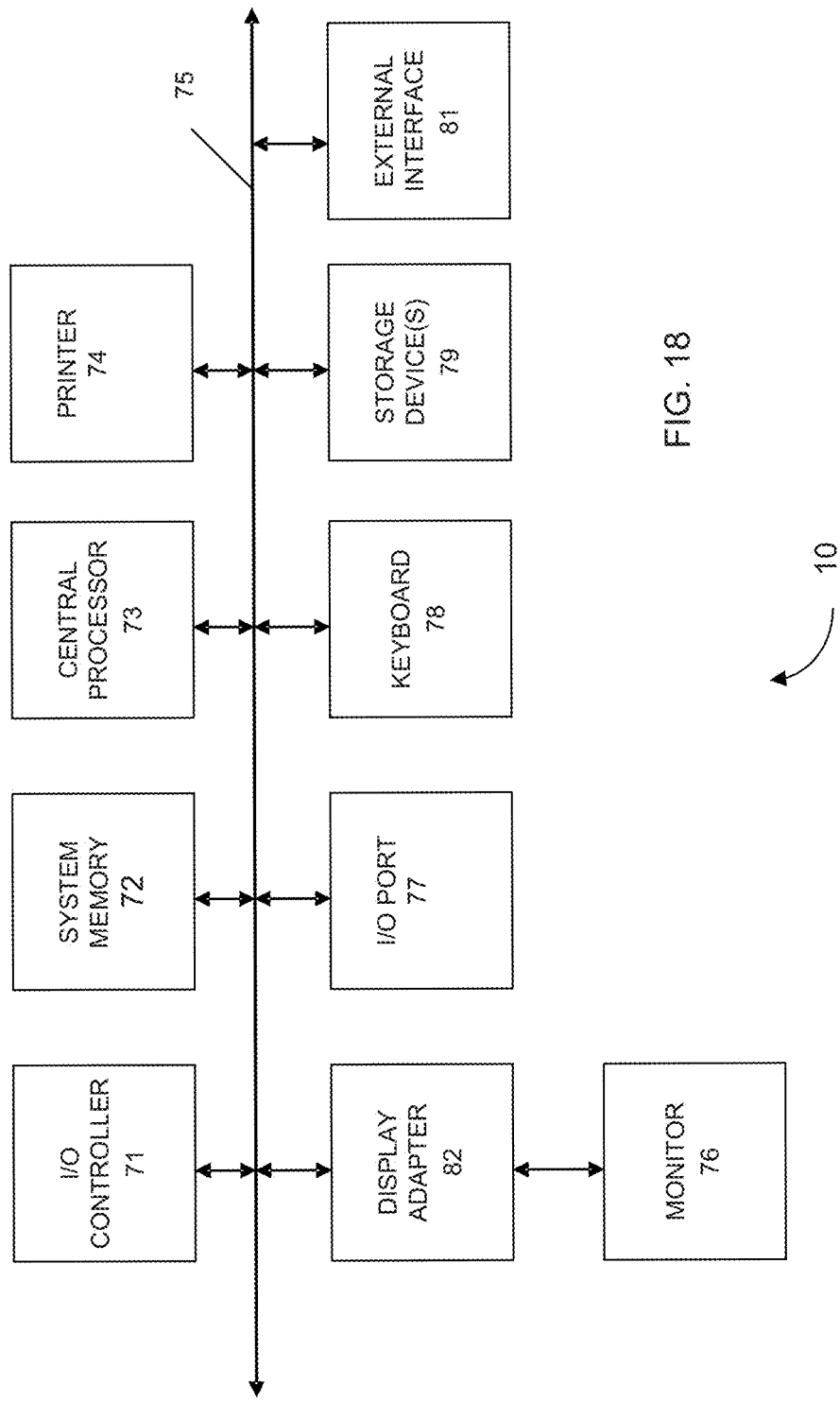
FIG. 18 shows a block diagram of an example computer system 10 usable with system and methods according to embodiments of the present invention.

Any of the computer systems mentioned herein may utilize any suitable number of subsystems. Examples of such subsystems are shown in FIG. 18 in computer apparatus 10. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 18 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®. For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive or optical disk), as well as the exchange of information between subsystems. The system memory 72 and/or the storage device(s) 79 may embody a computer readable medium. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method of determining a sequence of a first chromosomal region of an organism, the method comprising:
 receiving, at a computer system, sequence data from a sequencing of a plurality of nucleic acid molecules of the organism, wherein the sequence data for each of the plurality of nucleic acid molecules includes:
  one or more sequence reads of at least one portion of the nucleic acid molecule, and
  a label corresponding to the one or more sequence reads, the label indicating an origin of the nucleic acid molecule, wherein the sequence data includes at least 1,000 sequence reads;
 receiving, by the computer system, a first contig of the first chromosomal region;
 analyzing the at least 1,000 sequence reads to determine a group of sequence reads of the sequence data that overlap with an end sequence of the first contig, the group including sequence reads with a plurality of different labels indicating different origins of corresponding nucleic acid molecules, the different origins including different haplotypes; and
 extending, by the computer system, the first contig using the group of sequence reads of the sequence data that overlap with the end sequence of the first contig.

2. The method of claim 1, wherein extending the first contig includes:
 determining that the group of sequence reads has a first number of sequence reads at a next extension position that is less than a threshold number;
 forming one or more hypothesis sequences for extending the first contig;
 aligning other sequence reads to the one or more hypothesis sequences to identify at least the threshold number of sequence reads that overlap with the next extension position; and
 extending the first contig using at least the threshold number of sequence reads that overlap with the next extension position.

3. The method of claim 2, wherein the threshold number of sequence reads correspond to a same hypothesis sequence.

4. The method of claim 3, further comprising:
 determining whether at least the threshold number of sequence reads align to a second extension position of the same hypothesis sequence.

5. The method of claim 1, further comprising:
 determining an expected range for a number of labels of sequence reads corresponding to a correct branch for extending the first contig; and
 selecting, for extending the first contig, sequence reads of the first group that correspond to a first branch having a number of labels within the expected range as the correct branch.

6. The method of claim 1, further comprising:
 determining that the group of sequence reads that overlap with the end sequence of the first contig indicate an existence of a first allele and a second allele at a position in the first contig, each allele corresponding to a different branch for extending the first contig;
 determining a first number of labels that correspond only to the first allele;
 determining a second number of labels that correspond only to the second allele; and
 determining whether the position is heterozygous based on the first number and the second number.

7. The method of claim 6, wherein the position is identified as being heterozygous when both the first number and the second number are greater than a threshold.

8. The method of claim 1, further comprising:
 identifying sequence reads of the sequence data that align to the first contig and identifying the corresponding labels of the identified sequence reads, the corresponding labels forming a representative set of labels; and
 extending the first contig using sequence reads of the sequence data that overlap with the end sequence of the first contig and that have labels corresponding to the representative set of labels.

9. The method of claim 8, further comprising:
 identifying a set of sequence reads that overlap with the end sequence of the first contig;
 identifying a set of branches of the first contig, wherein a first subset of the overlapped reads correspond to a first branch and have a first set of tags, and wherein a second subset of the overlapped reads correspond to a second branch and have a second set of tags;
 determining a first number of tags shared between the representative set and the first set;
 determining a second number of tags shared between the representative set the second set; and
 using the first number and the second number to determine which branch is correct.

10. The method of claim 9, further comprising:
 selecting the first branch when the first number is larger than the second number.

11. The method of claim 9, further comprising:
 removing branches from the set of branches that have less than a specified number of corresponding sequence reads.

12. The method of claim 8, wherein the received first contig is a seed sequence, the method further comprising:
 determining the seed sequence.

13. The method of claim 12, wherein determining the seed sequence includes comparing a number of sequence reads from the sequence data that include the seed sequence to an expected number of sequence reads.

14. The method of claim 12, wherein determining the seed sequence includes comparing a number of labels corresponding to sequence reads of the sequence data including the seed sequence to an expected number of labels, wherein the expected number of labels is derived from a number of cells in a sample from which the plurality of nucleic acid molecules of the organism are sequenced.

15. The method of claim 8, further comprising:
identifying a first het at which overlapping sequence reads corresponding to the representative set of labels have two alleles;
unzipping the first contig to form a first haplotype sequence and a second haplotype sequence of the first contig;
identifying a first subset of the representative set of labels, the first subset corresponding to sequence reads having a first allele at the first het;
identifying a second subset of the representative set of labels, the second subset corresponding to sequence reads having a second allele at the first het;
using sequence reads having the first subset of labels to extend the first haplotype sequence; and
using sequence reads having the second subset of labels to extend the second haplotype sequence, wherein the method is performed by the computer system.

16. The method of claim 15, wherein the first subset of labels is greater than a specified number, and the second subset of labels is greater than the specified number.

17. The method of claim 15, further comprising:
identifying a first subset of a second set of labels corresponding to sequence reads having a first allele of a second het of the first contig; and
using sequence reads having the first subset of the second set of labels to extend the first haplotype sequence.

18. The method of claim 15, wherein the sequence reads of the sequence data correspond to both ends of a nucleic acid molecule, thereby forming a mate pair, the method further comprising:
extending the first haplotype sequence of the first contig using the mate pairs corresponding to the overlapping sequence reads having the first subset of the representative set of labels.

19. The method of claim 18, wherein extending the first haplotype sequence using the mate pairs includes:
extending the first haplotype sequence using a first sequence read of a mate pair; and
adding a second sequence read of the mate pair to an external cloud.

20. The method of claim 19, further comprising:
identifying a second set of labels corresponding to sequence reads of the sequence data that align to a reference sequence within a specified distance of the first contig; and
adding at least a portion of the sequence reads corresponding to the second set of labels to the external cloud.

21. The method of claim 19, further comprising:
adding the first sequence read to an internal cloud; and
extending the first haplotype sequence using the second sequence read by comparing a k-mer of the second sequence reads to k-mers of sequence reads of the internal cloud.

22. The method of claim 21, wherein comparing a k-mer of the second sequence reads to k-mers of sequence reads of the internal cloud includes:
comparing an index of k-mers of the second sequence to an index of k-mers of the internal cloud.

23. The method of claim 21, wherein the external cloud includes a plurality of k-mers for each sequence read added to the external cloud, the method further comprising:
removing a k-mer from the external cloud when the k-mer is used to extend the first haplotype sequence.

24. The method of claim 21, further comprising:
removing the first sequence read from the internal cloud when an end of the second sequence read is used to extend the first haplotype sequence.

25. The method of claim 21, further comprising:
removing the first sequence read from the internal cloud when an end of the first haplotype sequence extends a predetermined number of bases from a location that the first sequence read was used to extend the first haplotype sequence.

26. The method of claim 8, wherein each nucleic acid molecule includes a tag sequence indicating the origin of the nucleic acid molecule, wherein a same tag sequence on two nucleic acid molecules indicates a same origin for the two nucleic acid molecules, and wherein the label of the one or more sequence reads of a nucleic acid molecule corresponds to the tag sequence.

27. The method of claim 26, wherein the origin indicated by the tag sequence is an aliquot of a sample of the organism, the aliquot having less than a specified percentage of a genome of the organism.

28. The method of claim 26, wherein the origin indicated by a tag of a nucleic acid molecule is a non-cloned chromosomal fragment that is longer than the nucleic acid molecule and that includes the nucleic acid molecule.

29. The method of claim 1, wherein a number of bases that the first contig is extended is based on an amount of overhang of the overlapped reads of the group.

30. The method of claim 1, further comprising:
repeating extending the first contig using a new group of sequence reads that overlap with the end sequence of the first contig determined in a previous iteration.

31. The method of claim 1, wherein the plurality of nucleic acid molecules are fragments derived from longer molecules, the method further comprising:
adding the labels to the plurality of nucleic acid molecules such that at least a portion of the labels of nucleic acid molecules that are derived from a same longer molecule is shared.

32. A computer product comprising a non-transitory computer readable medium storing a plurality of instructions that when executed control a computer system to determine a sequence of a first chromosomal region of an organism, the instructions comprising:
receiving sequence data from a sequencing of a plurality of nucleic acid molecules of the organism, wherein the sequence data for each of the plurality of nucleic acid molecules includes:
one or more sequence reads of at least one portion of the nucleic acid molecule, and
a label corresponding to the one or more sequence reads, the label indicating an origin of the nucleic acid molecule, wherein the sequence data includes at least 1,000 sequence reads;
receiving a first contig of the first chromosomal region;
analyzing the at least 1,000 sequence reads to determine a group of sequence reads of the sequence data that overlap with an end sequence of the first contig, the group including sequence reads with a plurality of different labels indicating different origins of corresponding nucleic acid molecules, the different origins including different haplotypes; and
extending, by the computer system, the first contig using the group of sequence reads of the sequence data that overlap with the end sequence of the first contig.

* * * * *